US007004754B2

(12) United States Patent
Kaufmann et al.

(10) Patent No.: US 7,004,754 B2
(45) Date of Patent: Feb. 28, 2006

(54) AUTOMATIC CROWN AND GINGIVA DETECTION FROM THREE-DIMENSIONAL VIRTUAL MODEL OF TEETH

(75) Inventors: Markus Kaufmann, Berlin (DE); Peer Sporbert, Berlin (DE); Phillip Getto, Plano, TX (US)

(73) Assignee: OraMetrix, Inc., Richardson, TX (US)

( * ) Notice: Subject to any disclaimer, the term of this patent is extended or adjusted under 35 U.S.C. 154(b) by 194 days.

(21) Appl. No.: 10/626,796

(22) Filed: Jul. 23, 2003

(65) Prior Publication Data

US 2005/0019732 A1  Jan. 27, 2005

(51) Int. Cl.
*A61C 11/00* (2006.01)
(52) U.S. Cl. ..................................... 433/213
(58) Field of Classification Search ............... 433/213, 433/214, 215
See application file for complete search history.

(56) References Cited

U.S. PATENT DOCUMENTS

| | | | |
|---|---|---|---|
| 5,338,198 A | 8/1994 | Wu et al. | 433/213 |
| 5,879,158 A | 3/1999 | Doyle et al. | 433/24 |
| 5,975,893 A | 11/1999 | Chishti et al. | 433/6 |
| 6,015,289 A | 1/2000 | Andreiko et al. | 433/3 |
| 6,068,482 A | 5/2000 | Snow | 433/223 |
| 6,099,314 A | 8/2000 | Kopelman et al. | 433/213 |
| 6,227,850 B1 | 5/2001 | Chishti et al. | 433/24 |
| 6,334,853 B1 * | 1/2002 | Kopelman et al. | 600/590 |
| 6,371,761 B1 | 4/2002 | Cheang et al. | 433/24 |
| 6,386,878 B1 | 5/2002 | Pavlovskaia et al. | 433/215 |
| 6,409,504 B1 | 6/2002 | Jones et al. | 433/24 |
| 6,463,344 B1 | 10/2002 | Pavloskaia et al. | 700/98 |
| 2002/0102009 A1 | 8/2002 | Jones et al. | |
| 2002/0177108 A1 | 11/2002 | Pavlovskaia et al. | |
| 2003/0039389 A1 | 2/2003 | Jones et al. | |
| 2003/0039941 A1 | 2/2003 | Chishti et al. | |
| 2003/0235803 A1 * | 12/2003 | Nikolskiy et al. | 433/213 |

FOREIGN PATENT DOCUMENTS

WO     WO0180761     11/2001

OTHER PUBLICATIONS

S.M. Yammy and A.A. Farag, "A System for Human Jaw Modeling Using Intra-Oral Images", in Proc. *IEEE Eng. Med. Biol. Soc.* (*EMBS*) *Conf.*, vol. 20, Hong Kong, Oct. 1998, pp. 563-566.

M. Yammy, A.A. Farag, David Tasman, A.G. Farman, "A 3-D Reconstruction System for the Human Jaw Using a Sequence of Optical Images", *IEEE Transactions on Medical Imaging*, vol. 19, No. 5, May 2000, pp. 538-547.

* cited by examiner

*Primary Examiner*—Cary E. O'Connor
(74) *Attorney, Agent, or Firm*—McDonell Boehnen Hulbert & Berghoff LLP

(57) ABSTRACT

A method is provided for automatically separating tooth crowns and gingival tissue in a virtual three-dimensional model of teeth and associated anatomical structures. The method orients the model with reference to a plane and automatically determines local maxima of the model and areas bounded by the local maxima. The method automatically determines saddle points between the local maxima in the model, the saddle points corresponding to boundaries between teeth. The method further positions the saddle points along a dental arch form. For each tooth, the method automatically identifies a line or path along the surface of the model linking the saddle points to each other, the path marking a transition between teeth and gingival tissue and between adjacent teeth in the model. The areas bounded by the lines correspond to the tooth crowns; the remainder of the model constitutes the gingival tissue.

14 Claims, 28 Drawing Sheets

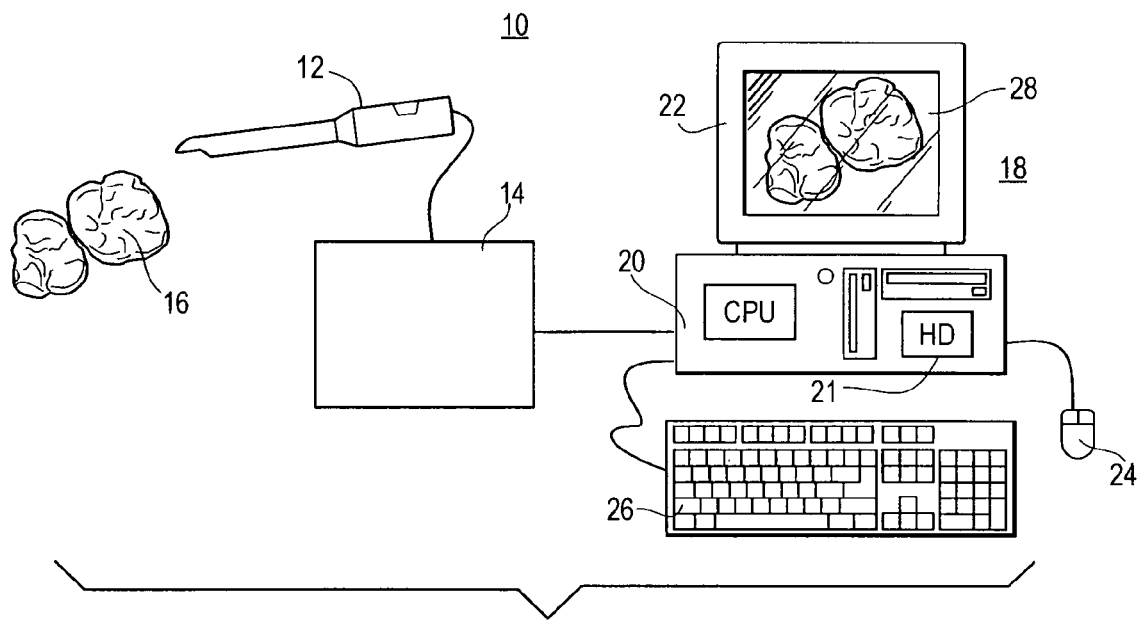
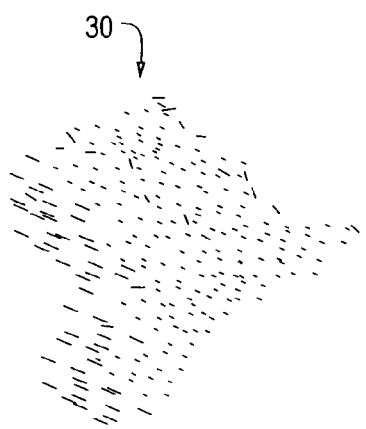
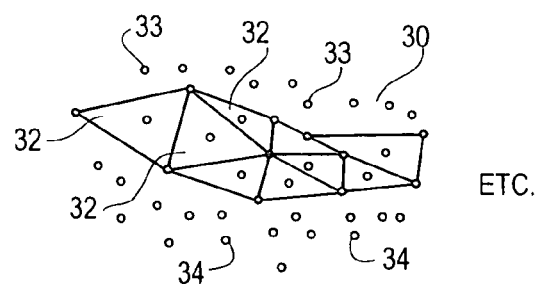

AUTOMATIC CROWN AND GINGIVA DETECTION FROM THREE-DIMENSIONAL VIRTUAL MODEL OF TEETH

This application is related to a patent application of Markus Kaufmann et al., filed on the same date as this application, entitled Method for Creating Single 3D Surface Model from A Point Cloud, Ser. No. 10/626,795, the entire contents of which are incorporated by reference herein.

BACKGROUND OF THE INVENTION

A. Field of the Invention

This invention is directed to an interactive workstation and associated computerized techniques for facilitating detection of individual teeth boundaries and gingival boundaries from a three-dimensional virtual computer model of teeth: The identification and separation of the teeth from the gingival tissue has applications in digital dentistry and orthodontics. For example, the separation of the teeth from the gingiva is typically a preliminary step in planning of treatment for orthodontic patients on a computer.

B. Description of Related Art

The traditional process of diagnosis and treatment planning for a patient with orthodontic problems or disease typically consists of the practitioner obtaining clinical history, medical history, dental history, and orthodontic history of the patient supplemented by 2D photographs, 2D radiographic images, CT scans, 2D and 3D scanned images, ultrasonic scanned images, and in general non-invasive and sometimes invasive images, plus video, audio, and a variety of communication records. Additionally, physical models, such as made from plaster of Paris, of the patient's teeth are created from the impressions taken of the patient's upper and lower jaws. Such models are manually converted into teeth drawings by projecting teeth on drawing paper. Thus, there is a large volume of images and data involved in the diagnosis and treatment planning process. Furthermore, the information may require conversion from one form to another and selective reduction before it could become useful. There are some computerized tools available to aid the practitioner in these data conversion and reduction steps, for example to convert cephalometric x-rays (i.e., 2 dimensional x-ray photographs showing a lateral view of the head and jaws, including teeth) into points of interest with respect to soft tissue, hard tissue, etc., but they are limited in their functionalities and scope. Even then, there is a fairly substantial amount of manual work involved in these steps.

Additionally, the physical molds of the patient's dentition are converted into physical models such that each tooth can be moved and repositioned individually. However, such models allow free movement of teeth without regard to the patient's biological constraints, and can frequently lead to impractical treatment set-ups.

Furthermore, a number of measurements, e.g., available space between teeth, are also often done manually. Generally, these steps are time consuming and prone to inherent inaccuracies. Furthermore, the practitioner has to contend with the biological interdependencies within the patient, which introduces constraints eliminating certain treatment options that would otherwise be acceptable, between the soft tissue, the hard tissue, and the teeth. There is lack of an integrated platform which a practitioner could utilize to filter-out non-practicable treatment options.

Consequently, the practitioner is left to mental visualization, chance process to select the treatment course that would supposedly work. Furthermore, the diagnosis process is some-what ad-hoc and the effectiveness of the treatment depends heavily upon the practitioner's level of experience. Often, due to the complexities of the detailed steps and the time consuming nature of them, some practitioners take a short cut, relying predominantly on their intuition to select a treatment plan. For example, the diagnosis and treatment planning is often done by the practitioner on a sheet of acetate over the X-rays. All of these factors frequently contribute towards trial and error, hit-and-miss, lengthy and inefficient treatment plans that require numerous mid-course adjustments. While at the beginning of treatment things generally run well as all teeth start to move at least into the right direction, at the end of treatment a lot of time is lost by adaptations and corrections required due to the fact that the end result has not been properly planned at any point of time. By and large, this approach lacks reliability, reproducibility and precision. More over, there is no comprehensive way available to a practitioner to stage and simulate the treatment process in advance of the actual implementation to avoid the often hidden pitfalls. And the patient has no choice and does not know that treatment time could be significantly reduced if proper planning was done.

In recent years, computer-based approaches have been proposed for separating teeth in patient's 3D dentition model. A 3D scanned model of a patient's dentition, whether taken in-vivo or from a physical model, typically covers the surfaces of all teeth and parts of the surrounding gum, but there can also be gaps in it, i.e. parts of teeth and gum the 3D scan did not reach. Given this data, the present invention is directed to a procedure to analyze the data and to determine which portions of the scanned data correspond to the gums and which portions correspond to the individual. Thus, both the transitions between the teeth and the gums and those between adjoining teeth are detected, and the portions between these transitions are correctly assigned to the corresponding portions of the scanned jaw.

Cheang et al., U.S. Pat. No. 6,371,761, describe a method using flexible plane for separating teeth wherein a computer-implemented method separates first and second portions of a tooth by defining a cutting surface intersecting the first and second portions; and applying the cutting surface to the to the tooth to separate the tooth into two portions. Pavlovskaia, et al, U.S. Pat. No. 6,386,878, and U.S. Patent Application Publication 2002/0177108 describe a method using cutting surface for removing gingival tissue from teeth wherein a computer-implemented method removes gingival from a model of a tooth by defining a cutting surface along the gingiva; and applying the cutting surface to the to the tooth to separate the gingival from the in a single cut. Jones et al., U.S. Pat. No. 6,409,504, and in related U.S. Patent Application Publication 2003/0039389, and U.S. Patent Application Publication 2002/0102009, describe a method for manipulating a digital dentition model to form models of individual dentition components wherein computer-automated techniques are described using "voxel representation" and "geometric representation" of a 3D model. Pavlovskaia, et al, U.S. Pat. No. 6,463,344, describe a computer-implemented method that generates a computer model of one or more teeth, by receiving as input a digital data set of meshes representing the teeth; creating a parametric representation of the digital data set; and displaying the computer model of the teeth using the parametric representation. Chisti et al, U.S. Published Patent Application 2003/0039941, describe digitally modeling the deformation of gingival tissue during orthodontic treatment.

In recent years, computer-based approaches have been proposed for aiding orthodontists in their practice. However, these approaches are limited to diagnosis and treatment planning of craniofacial structures, including the straightening of teeth. See Andreiko, U.S. Pat. No. 6,015,289; Snow, U.S. Pat. No. 6,068,482; Kopelmann et al., U.S. Pat. No. 6,099,314; Doyle, et al., U.S. Pat. No. 5,879,158; Wu et al., U.S. Pat. No. 5,338,198, and Chisti et al., U.S. Pat. Nos. 5,975,893 and 6,227,850, the contents of each of which is incorporated by reference herein.

A method for generation of a 3D model of the dentition from an in-vivo scan of the patient, and interactive computer-based treatment planning for orthodontic patients, is described in published PCT patent application of OraMetrix, Inc., the assignee of this invention, publication no. WO 01/80761, the contents of which are incorporated by reference herein. The PCT application, at pages 73 and 75, describes several methods for separating teeth from a virtual model, using user interaction and virtual tooth models. The application suggests that tooth separation could be done using an automated algorithm looking for grooves between tooth crowns and gingival tissue, but does not describe what that algorithm might be or describe how the process would work.

Other background references related to capturing three dimensional models of dentition and associated craniofacial structures include S. M. Yamany and A. A. Farag, "A System for Human Jaw Modeling Using Intra-Oral Images" in *Proc. IEEE Eng. Med. Biol. Soc.* (*EMBS*) *Conf.,* Vol. 20, Hong Kong, October 1998, pp. 563–566; and M. Yamany, A. A. Farag, David Tasman, A. G. Farman, "A 3-D Reconstruction System for the Human Jaw Using a Sequence of Optical Images," *IEEE Transactions on Medical Imaging,* Vol. 19, No. 5, May 2000, pp. 538–547. The contents of these references are incorporated by reference herein.

SUMMARY OF THE INVENTION

A method is provided for automatically identifying or determining tooth crowns in a virtual three-dimensional model of teeth and associated anatomical structures (e.g., gingival tissue) in a dental arch. Separation of such teeth into independent virtual objects is useful for a variety of purposes, including moving the virtual tooth objects relative to each other to simulate treatment of a patient, such as simulate orthodontic treatment.

The method includes the step of storing the model in a memory accessible to a general-purpose computer. The computer including a processing unit. The method includes the step of providing machine-readable instructions for execution by the processing unit. The instructions operate on the model in the following respects:

1) orientating the model with reference to a plane;
2) automatically determining local maxima of the model and areas bounded by the local maxima;
3) automatically determining saddle points between the local maxima in the model, the saddle points corresponding to boundaries between teeth;
4) determining the position of the saddle points along a dental archform, and
5) for each tooth, automatically identifying a line or path linking the saddle points to each other, the lines marking a transition between teeth and gingival tissue and between adjacent teeth in the model, and identifying areas bounded by the lines and in the direction of the plane as corresponding to the tooth crowns.

Since the process for detection of crowns identifies lines defining the transition between the teeth and gingival tissue, the identification of the teeth necessarily results in identification of the gingival tissue as well. In particular, the gingival tissue will ordinarily comprise the portion of the model in the areas bounded by the lines and in the direction away from the plane.

In yet another aspect of the invention, it will also be appreciated that we have described a ravine detection invention that provides instructions for execution by a programmed computer that identifies a path interconnecting saddle points between virtual teeth in a virtual model of the dentition. The path comprises a transition between teeth and gingival tissue and between adjacent teeth in a virtual model of dentition. In a preferred embodiment, as explained in FIG. 16, the path is determined by performing a tree search, and wherein the tree search is performed by reference to local curvature of the virtual model and a vector field for the model defining a direction of search for the path.

BRIEF DESCRIPTION OF DRAWINGS

FIG. 1 is a schematic diagram of one possible environment in which the invention can be practiced, showing a scanner that scans a set of teeth and associated gingival tissue, either in vivo or from a physical model, and a computer which stores scan data in the form of a cloud of three dimensional points and generates a single mesh surface representation of the scanned object.

FIG. 2 shows a cloud of points that are stored in a computer and which represent the three-dimensional surface of the object scanned in FIG. 1.

FIG. 3 shows a surface consisting of adjacent triangles that represent a portion of the surface of the object of FIG. 2, indicating in a some what simplified manner the objective of the present invention to provide a single surface representing the object from a cloud of points, and presenting a weighted average of all the points in the point cloud.

In FIG. 20, the arch form comprises a parabolic coordinate system which is used to determine the position the saddle points along the arch form, corresponding to step 310 of FIG. 11.

DETAILED DESCRIPTION OF THE PREFERRED EMBODIMENT

Figure 4A:
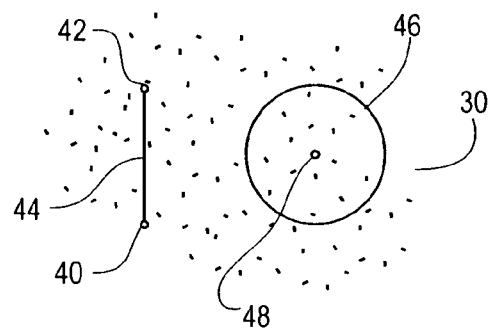
FIGS. 4A–4G shows how the surface of FIG. 3 is constructed from a cloud of points, and showing several different methods by which a new triangle is formed.

FIG. 1 is a schematic diagram of one possible environment in which the invention can be practiced. A scanner 10 consisting of an optical probe unit 12 and scanner electronics module 14 conducts a 3D scan of an object 16. The object 16 can be virtually anything. In the present example the object 16 consists of a dentition. The scan of the dentition and gum tissue could be obtained either in-vivo, or it could be made from a physical model of the dentition and associated anatomical structures. The present invention is not limited to the particular manner in which the virtual model of the dentition and gingival tissue is obtained. For example, the scanner could be a laser scanner or destructive scanner. In the illustrated embodiment, the scanner is a hand-held in-vivo scanner as described in the published PCT application of OraMetrix, publication no. WO 01/80761, the contents of which are incorporated by reference herein. An opaquing solution may be applied to the surface to the dentition to enhance the ability to scan an objection in a "wet-field" environment, as taught in the patent application of Nancy Butcher et al., Ser. No. 10/099,042, filed Mar. 14, 2002, now issued as U.S. Pat. 6,854,973, the contents of which are incorporated by reference herein.

The scanner 10 obtains scan data describing the surface configuration and shape of the dentition 16. The scanner electronics module 14 includes a programmed computer that converts data from the probe 12 into a point cloud, each point in the cloud having three-dimensional coordinates corresponding to a point on the surface of the object. The above-cited PCT application contains a description of a method of generating point cloud data, in a form of a series of individual three-dimensional "frames", which are in turn registered to each other in a best fit manner to form a complete 3D point cloud model of the object. The reader is directed to the PCT document for a description of the generation of the point cloud. The scan data is transmitted to a general-purpose computer 18, which includes a central processing unit 20, a hard disk memory 21, and a user interface consisting of a monitor or display 22, a mouse 24, and keyboard 26. The scan data (point cloud) is stored in the hard disk memory 21 of the computer. The computer also includes machine executable instructions, described herein, for processing the points in the point cloud and generating a single mesh surface configuration representing a three-dimensional virtual model of the dentition and gingival tissue. The virtual model comprising the single mesh surface of the dentition is shown displayed on the computer monitor 22, as indicated at 28. The mouse and keyboard provide a means by which the user accesses the 3D surface generation software and initiates the processing, and then manipulate, study, measure, or otherwise use the resulting 3D surface.

As noted above, a method is described herein for automatically identifying tooth crowns in a virtual three-dimensional model 28 of teeth in a dental arch. The method includes a step of storing the model in a memory accessible to a general-purpose computer, such as the hard disk memory 21 of FIG. 21. The computer includes a processing unit or CPU 20 which executes machine readable instructions, stored in memory of the computer, that operate on the model in several operations or processes. These processes include a step of orientating the model with reference to a plane; determining local maxima of the model (corresponding to high points or cusps of teeth) and areas bounded by the local maxima ("catchment areas" herein); automatically determining saddle points between the local maxima in the model, the saddle points corresponding to boundaries between teeth; determining the position of the saddle points along a dental arch form; and, for each tooth, automatically identifying a line or lines defining a path linking the saddle points to each other, the path comprising a transition between teeth and gingival tissue and between adjacent teeth in the model, and identifying areas bounded by the lines as crowns of teeth (and, consequently also identifying the gingival tissue).

As noted above, the method of the present invention is capable of executing in a fully automated manner, with no user involvement. Depending on the quality of the scan data, the method may benefit from some user involvement, as will be described below. The method will be described more particularly in conjunction with FIGS. 11–26, which describe the preferred embodiment of the method in flow chart form and show screen shots from the display of the computer showing the results of some of the processing steps in the method.

The initial step in the process, orienting the model with respect to a plane, can be done with either the initial point cloud or a representation of the point cloud as a single continuous surface or mesh. The remaining operations are ideally performed on a single continuous mesh surface. Hence, a processing step is performed of converting the point cloud model to a single surface representation. The process of converting a point cloud to a single mesh surface will be described initially in conjunction with FIGS. 2–10E, and then the present discussion will revert to a description of the remainder of the processing steps and the discussion of FIGS. 11–26.

Conversion of Point Cloud to Single Mesh Surface

FIG. 2 shows an example of a 3D point cloud 30 that may be captured by the scanner of FIG. 1. FIG. 3 shows a close-up view of a portion of the point cloud 30. In the present example, the point cloud 30 consists of thousands or even millions of individual points in three-dimensional space. Depending on the quality of the scanner or the scanning, the model may have lots of noise in the form of stray points, it may be inhomogeneous, and it may have many points at different depths over a given area, such that selection of a points to use to construct a surface model is difficult. This is particularly so if the source data is obtained from a cumulatively registered model constructed from hundreds or thousands of individual frames (each frame covering only a portion of the object). Each of these individual frames consists of 3D measured points and triangles which reference these measured points, each triangle linking points that lay next to each other in the 3D surface or mesh. Owing to measuring errors and errors during registration, the points of a registered scan form a noisy cloud of points along the virtual surface of the scanned object. The point density on a certain area of the surface is dependent on the number of individual frames carried out on this area (=number of triangle layers on this area) and on the recording angle of these individual scans.

The object of the procedure is to generate from this cloud of points a new boundary or surface representation consisting of points and triangles which, as far as possible, consists exactly of one layer on every area of the surface of the scanned object. This is indicated in FIG. 3 by the continuous triangle surface. Preferably, the point density in the surface representation depends not on the point density of the source data, but on the surface curvature. This way, a maximum measure of data reduction is to be achieved with a minimum measure of distortion of the source data. Further analysis and processing of the 3D data is facilitated by replacing the original data (point cloud), consisting of locally limited surface portions with multiple-layer overlapping, with the new surface configuration, consisting of a single-layer surface which has both a maximum measure of coherence, and which also represents a surface in the topological sense. This is shown in a somewhat simplified form in FIG. 3: from the cloud of points 30, a new surface consisting of connecting, adjacent triangles 32 is constructed. Points in the original cloud of points include both points 33 and 34 above and below the surface, respectively. As will be explained below, the surface consisting of triangles 32 (or, equivalently, the associated set of points forming the vertices of these triangles) represents a weighted average of the point cloud. Further processing or analysis of the surface consisting of triangles 32 is much easier and efficient than processing the entire point cloud 30.

In general, the vertices of the triangles 32 forming the single mesh surface are not points in the point cloud, but rather they are newly-constructed vertices formed as a weighted average of a set of nearby points that satisfy selection criteria; moreover, the vertices of the triangles are tested against rejection criteria described herein in order to insure that the triangle surface conforms to the point cloud with a minimum of deviation. The manner of selecting the set of points used to construct the new vertices of the triangles 32 and testing the new vertex to see if it should be used are explained in detail in conjunction with FIGS. 10A–10E.

Referring now to FIG. 4A–4G, a method will now be described for constructing a surface from a cloud of points in a preferred embodiment of the invention. As noted earlier, each point in the cloud of points is assigned three-dimensional spatial coordinates. The cloud of points and the three-dimensional coordinates of the points can be obtained using any method, one possibility is scanning the object with a 3D scanner (such as an optical or laser scanner) and storing the scan data in memory. The nature of the representation of the cloud of points is not particularly important.

The method includes the step of storing the cloud of points in a memory (e.g., hard disk 21) of a computer 18. The method further includes the step of providing machine-executable instructions for the computer that operate on the cloud of points 30. The instructions construct an initial triangle from the cloud of points. This will be described in conjunction with FIGS. 4A and 4B below. In one embodiment, the initial triangle consists of two points from the cloud of points and a third point, which could either be a third point in the cloud of points or more preferably a point selected as a weighted average of a set of points in the vicinity of the two points, and in which the selection criteria for the set of points used to construct the third point satisfies selection criteria described later in this document.

The method continues with constructing a multitude of adjacent triangles forming a single continuous surface representing the object. Preferred methods will be described in more detail below in conjunction with FIGS. 4C–4G. As shown in the figures, the triangles comprise planar surfaces having three vertices. The vertices of the adjacent triangles comprise the three points forming the initial triangle plus a remainder of points, each computed as a weighted average of nearby points in the cloud of points and in which the selection criteria for the points forming the vertex and the testing of the vertex against rejection criteria is satisfied. As such, the final surface representation is a weighted average surface representation which requires much less data to represent the surface than the initial point cloud, since it reduces the number of points to represent the surface down to only the vertices. Since each vertex (other than the vertex of the initial triangle) is a weighed average of nearby points, the final surface configuration is a weighted average surface.

Referring now in particular to FIG. 4A, a portion of the point cloud 30 is shown. The manner of selecting the initial triangle will be described first. The preferred embodiment makes use of the following features, stored as memory files: a list of all the points in the point cloud, each point associated with both three dimensional coordinate (X, Y, Z) values and an index (number, e.g., point number); a list of all "open edges", as defined herein; a list of all the "closed edges", defined herein, and a list of all triangles that are created by the process which form the single mesh surface.

The process starts by selecting a first point 40. The first point may be any randomly selected point in the point cloud, the first point (index=1), the last point (index=n, where n is the number of points in the point cloud), or otherwise. The method continues by selecting a second point 42, which may also be a point in the point cloud. The point 42 could be selected in a variety of possible methods, such as any point in the point cloud that has a distance from the first point 40 that does not exceed a specified threshold; a point having the closest index number to the index number of the first point, or the point could be constructed from averaging X, Y and Z values from set of points in the vicinity of the first point 40. (The first point could similarly be selected).

After the first two points are selected, an edge 44 is constructed joining points 40 and 42. The task is now to select a third point forming the third vertex of the first triangle. In a preferred embodiment, a third point 46 is selected as a weighted average of points in a region that is a certain distance way from the edge 44, not too close, not too far (the distance criterion could also use the first and second points instead of the edge). The aim here in selection of the third point (or, more generally, any new point forming a vertex of a triangle in the surface after creation of the initial triangle) is to continue as homogeneously as possible the existing surface structure (the single mesh that has already been generated) and ensure that the deviation between the surface generated with the new point and the source data points is kept to a minimum. The minimization of the deviation is achieved by using a weighted mean of all source data points to select the third point 46. Here, a weighted mean of all source data points is formed for this purpose, which do not exceed a certain maximum distance from the edge 44 and which are not located in certain exclusion areas. These exclusion areas comprise all areas located "behind" the edge (to the left of the edge 44) or behind the neighboring edges—and hence within one of the triangles referencing one of the points of the edge. The points are weighted such that those points that contribute to the formation of a triangle whose sides are as equal as possible are assigned the greatest relative weight. But if the mean variation of the normals of the source data points involved (measure of surface curvature) or the angle of the triangle formed with the aid of the new point with the other triangle of the open edge exceeds a threshold value, then the point is rejected, because excessive deviation of the new triangle from the source data points is to be expected. In this case the formation of the mean value is repeated, the weights being changed in favor of a smaller triangle. If the procedure is successful, a new triangle which references the two points of the open edge and the new point is formed and the list of the open edges is updated accordingly. The process of selecting the initial third point and all the new vertices forming the single continuous surface will be explained further in conjunction with FIGS. 10A–10E below. The procedure is not successful if there are no or too few source data points in the vicinity of the edge which satisfies the selection criteria. In this case the edge 44 remains "open."

Figure 4B:
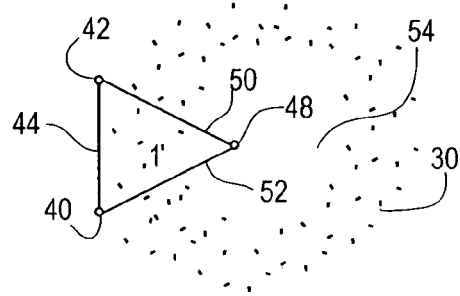

This can be seen in the example of FIGS. 4A and 4B. The points in the area bounded by the curve 46 are used in this example, the boundary 46 including points that are within a pre-set maximum distance from the edge 44. The points may also be away from the edge by a pre-set minimum amount. A weighted averaging of the points in the region is performed and the resulting weighted average of X, Y and Z values are used to construct a new point 48. The resulting triangle 1 has sides or edges 50 and 52. These edges 50 and 52 are added to the list of open edges stored in memory. The points in the region 46 that were weighted to arrive at point 48 are "deleted" from the list of points, as indicated by the void 54 of points indicated in FIG. 4B. By "deleted", we mean that the points are marked such that the points are not used further in the modeling procedure. The underlying points in the point cloud are not actually "deleted" in the literal sense.

Figure 4C:
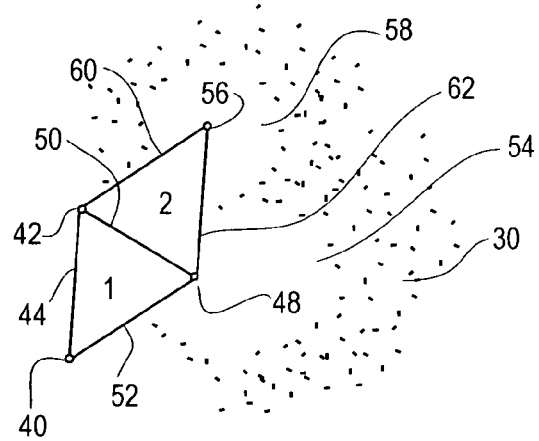

The process proceeds by selecting another open edge, for example edge 50, and constructing a new triangle formed by the edge 50 and another point derived from the point cloud. The area within triangle 1 is in an exclusion area, so the algorithm seeks points in the "front of the edge", or to the upper right of triangle 1 in FIGS. 4B and 4C. A weighted average of points in the boundary of points to consider for the open edge is performed, and the result is the selection of a new point 56, shown in FIG. 4C, provided the new vertex 56 satisfies a selection criterion described below in FIG. 10E, i.e., the angle between a surface normal vector from triangle 2 and the surface normal vector of triangle 1 does not exceed a predefined threshold value. The set of points in the point cloud used to select point 56 are "deleted" from the cloud of points, indicated by the void 58. Now, new triangle 2 is constructed, consisting of original point 42, and new points 48 and 56. The new triangle 2 has open edges 60 and 62, while edge 50 is deleted from the "open edge" list and instead is added to the "closed edge" list. As will be appreciated from the above examples, an "open edge" is a line segment joining two points forming an edge of a triangle in the surface model, which is shared by only one triangle, for example edge 52 or edge 44. Conversely, a "closed edge" is one in which the edge is common to two triangles, such as edge 50 in FIG. 4C.

Figure 4D:
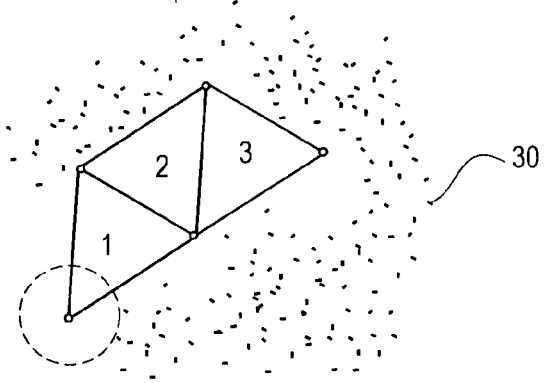
Figure 4E:
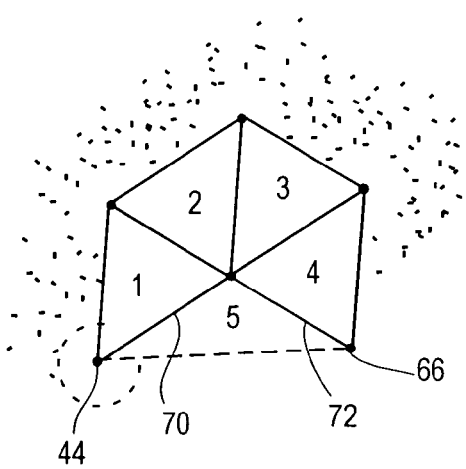

The process of selecting new points and triangles continues as shown in FIGS. 4D and 4E, showing the construction of triangles 4 and 5. As shown in FIG. 4E, a triangle can also be formed by connecting two points 40 and 66 of different triangles, in which the included angle of the open edges that join the two triangles (edges 70 and 72 in FIG. 4E) meets some requirement or rule, such as the included angle is an acute angle (less than 90 degrees, a preferred embodiment for the teeth application), the included angle is less than 145 degrees, or the included angle is less than 180 degrees, or the length of the new edge is less than a pre-set maximum distance.

Figure 4F:
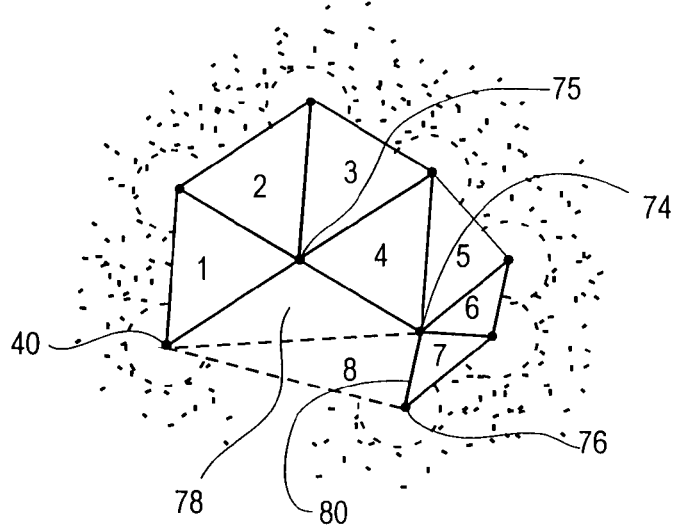
Figure 4G:
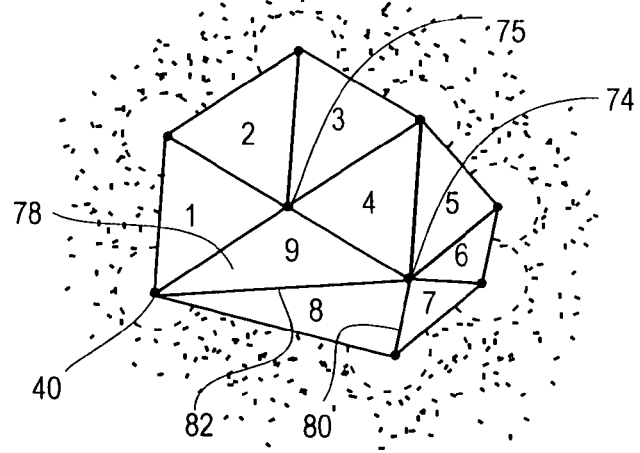

FIGS. 4F and 4G show another example of how triangles may be created from existing points in the surface. The surface consists in this situation seven triangles, numbered 1–7. Triangle 8 is constructed by connecting existing vertices 74, 76 and 40. This forms a hole 78. The hole is assigned a triangle by connecting points 74, 75 and 40. Edge 82 is common to triangles 8 and 9 and is deemed a closed edge.

Thus, in a preferred embodiment, the process includes instructions for forming triangles from either the point cloud or previously identified vertices in the surface. The algorithm generally generates, in succession, either:

2 new points (=starting edge of a triangle), as in FIG. 4A; or 1 new point and 1 triangle consisting of this point and 2 points identified in an earlier step (FIG. 4C, the selection of new point 56 forming the second triangle); or 1 triangle which references 3 points generated in an earlier step (e.g., the generation of the triangle 5 in FIG. 4E, or the generation of triangles 8 and 9 in FIGS. 4F and 4G).

Thus, at the time of its generation, each triangle (except the first or starting triangle) has at least one common edge with a triangle generated in an earlier step. A list of "open edges" of all triangles already generated is kept for this purpose. New triangles are always formed along these edges (exception: starting triangles), i.e., such an open edge is selected for generating a new triangle. Whether a point and a triangle or only a triangle from exiting triangles, will be formed is determined by rules that are coded in the software, such as by the angle of this edge with the neighboring open edges, by other open edges that may exist in the neighborhood and by the point distribution of the source data near the edge.

As indicated by the voids in the point clouds in FIGS. 4B–4G, all source data points involved in forming a new vertex of a triangle in the surface are "deleted" i.e., are marked to exclude them from the rest of the modeling procedure.

The preferred embodiment includes rules for generating triangles without generating a new point, i.e., from existing vertices of triangles already created. In a first possible rule, new triangles could be created when two adjacent open edges together form acute angle. A triangle can be formed in this case, which is situated between these two edges, i.e., which references the 3 points of the two edges. In a refinement of this rule, this triangle is formed only if the mean distance between the source data points located above (or below) this triangle and the triangle area does not exceed a certain threshold.

As a second possibility, a triangle can be created when point of another open edge lies near the open edge (and in front of it). This is the example of creating triangle 8 in FIG. 4G. In this case a triangle can be formed which references the open edge 80 and this third point 40. But just as in the previous case, this triangle (8 in FIG. 4G) is generated only after the measurement of the distance has been carried out successfully. This way of forming triangles is the basis for the "growing together" of the single mesh, i.e., for enabling it also to render cylindrical, spherical or other topologies.

As a third possible example, triangles are constructed to fill holes, that is when three open edges together limit a triangular hole. The hole is closed by a triangle which references the three vertices of these three edges.

Figure 5:
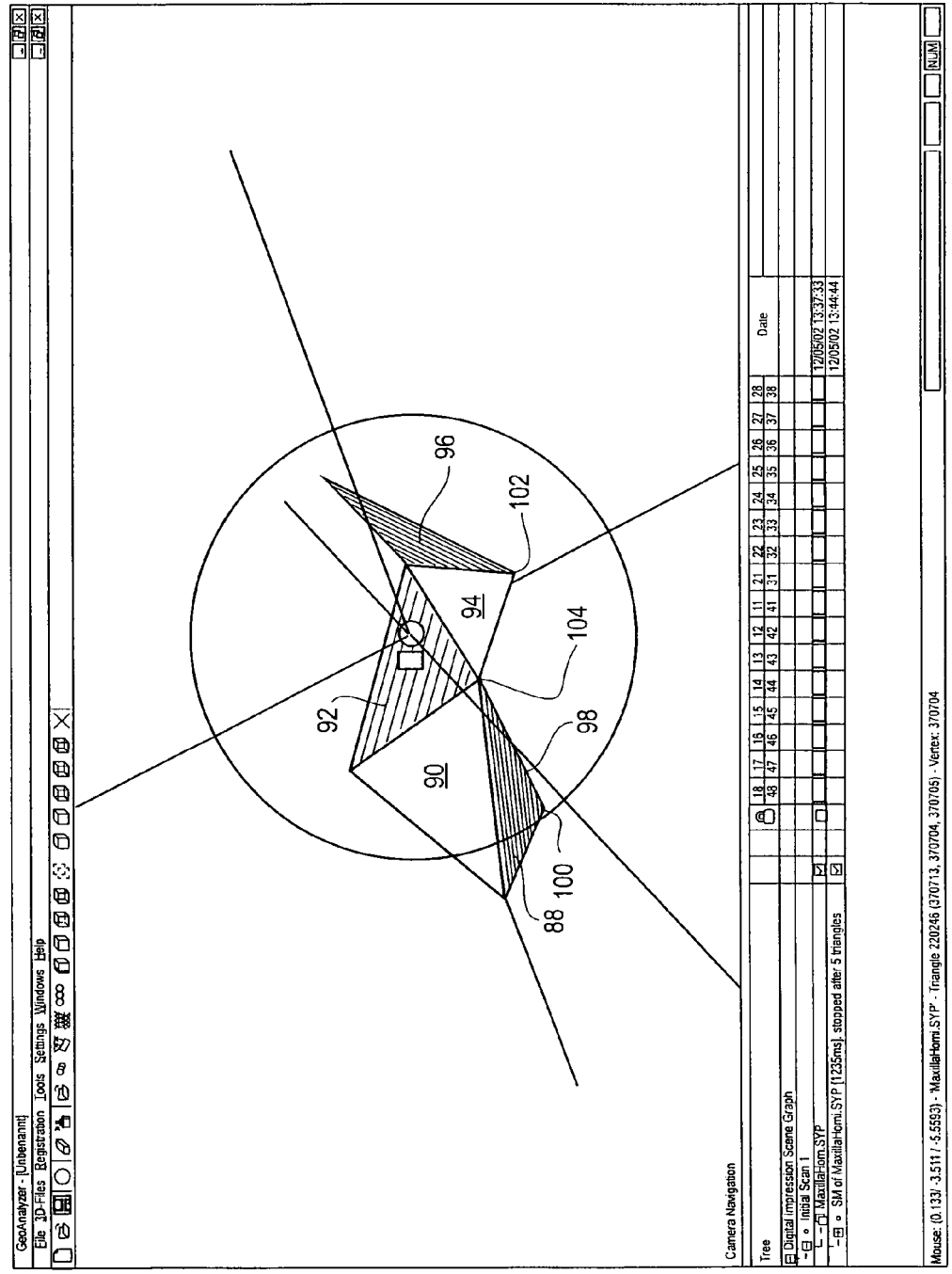
FIGS. 5, 6 and 7 shows how new triangles are constructed in the computer in three dimensions.
Figure 6:
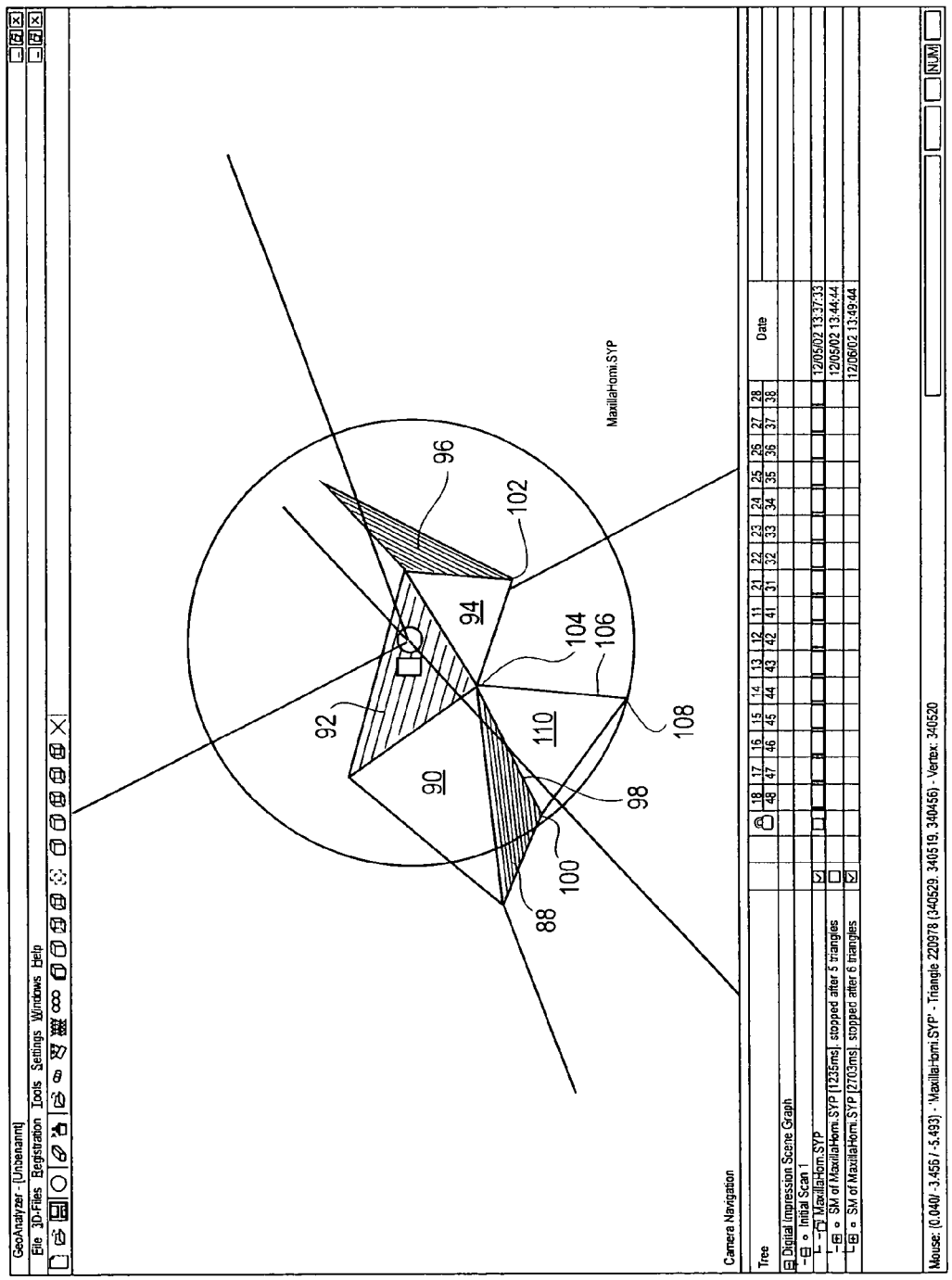
Figure 7:
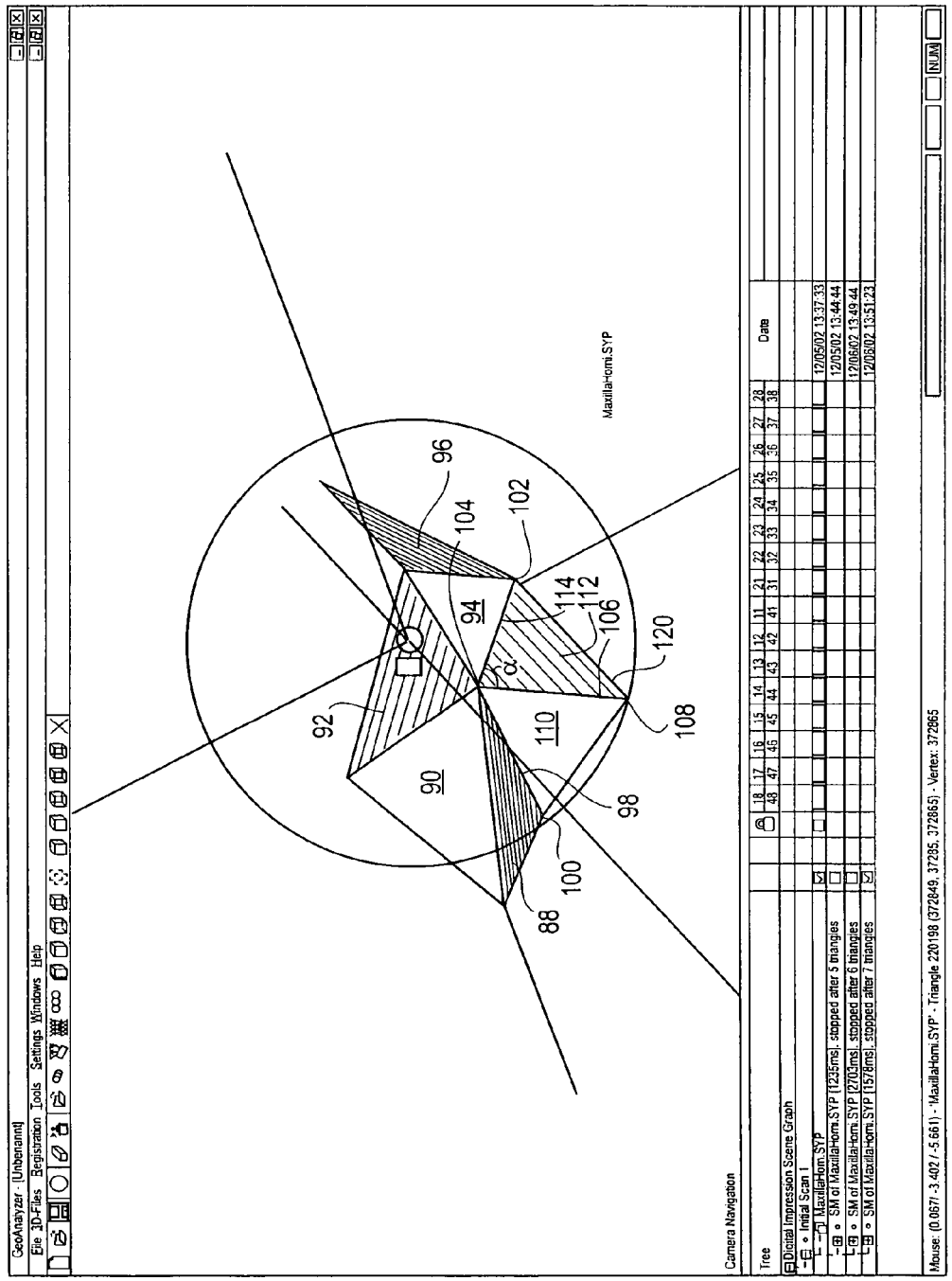

FIGS. 5, 6 and 7 shows how new triangles are constructed in the computer in three dimensions. FIG. 5 shows points in a point cloud and a single continuous triangle surface consisting of triangle surfaces 88, 90, 92, 94, 96. Edge 98 is an open edge and is the open edge that is selected to form a new triangle. In the present example, the rules for generating triangles would not permit a triangle to be formed by connecting vertices 100 and 102 since the distance between the two vertices exceeds a threshold. Therefore, the process will create a new vertex from the points in the point cloud, which will be part of a triangle containing points (vertices) 100 and 104 and include the open edge 98. Thus, as described above, a weighted average of points is performed for points within a threshold distance from the open edge 98 and a new vertex is created. The new vertex is shown in FIG. 6 as point 108. This point 108, along with points 100 and 104, creates the new triangle surface 110 having an open edge 106.

Referring now to FIG. 7, the next open edge to check is edge 106. Under the rules for generating triangles that are coded in software, the process looks to see if a triangle can be formed from existing vertices using the open edge 106. In this case, we have vertices 102, 104 and 108. The included angle α between open edges 106 and 114 (sharing a common vertex 104) meets the requirements of the rule for generating triangles from adjacent open edges since angle α is acute (less than 90 degrees). Therefore, a new triangle surface 112 is formed joining vertices 102, 104 and 108. The process continues by selecting another open edge, such as edge 120 of triangle 112, and applying the rules for generating triangles from the open edge 120.

Figure 8:
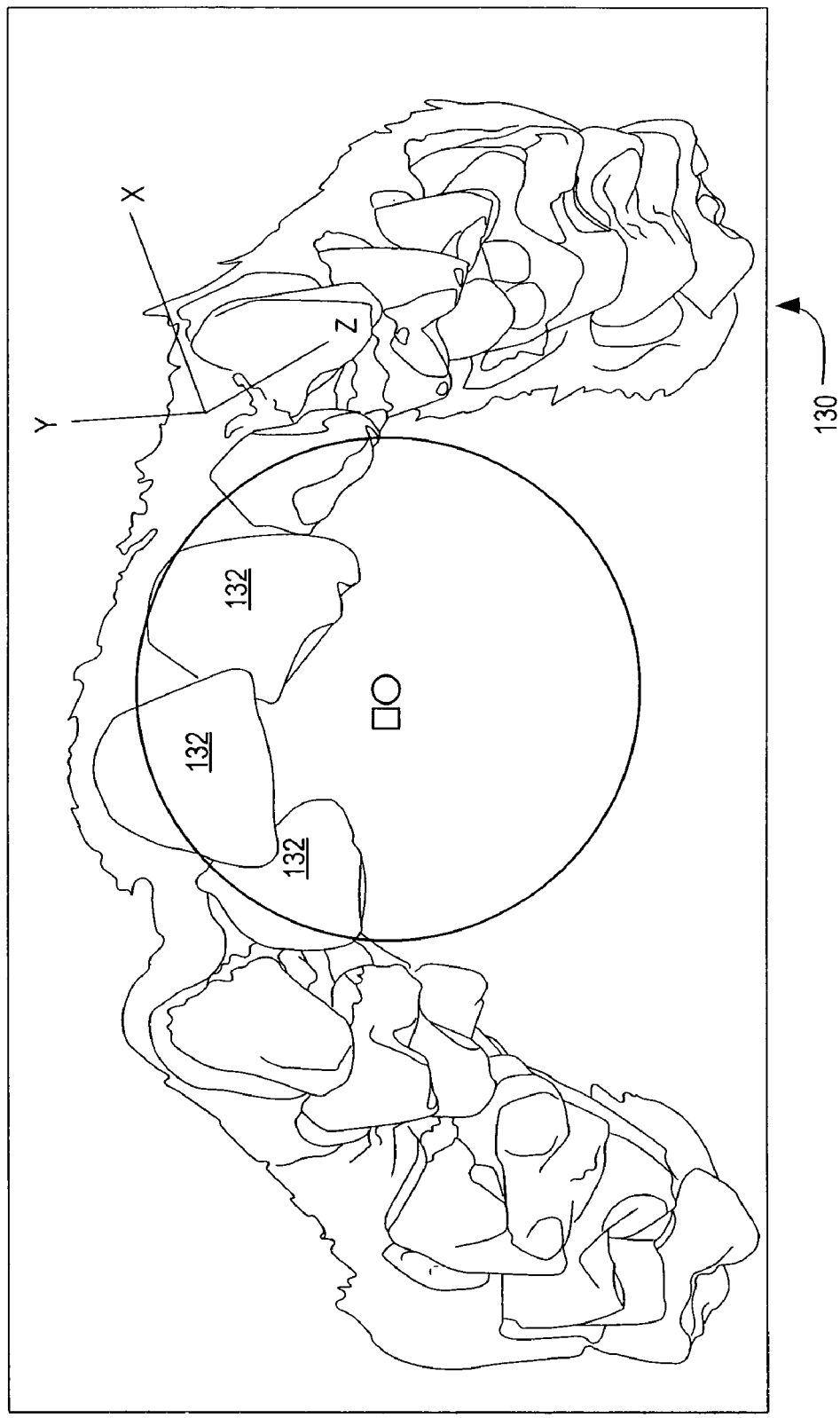
FIG. 8 shows a complete 3D model of the upper arch, including teeth, of a human as it might be displayed on a monitor of a general purpose computer, after in-vivo scanning of the arch; the scanning is used to create a cloud of points and the execution of the methods of the present invention take the resulting cloud of points and create a single 3D surface presenting the anatomical structures of the upper arch.

As noted earlier, the process of constructing a single mesh surface can be used for any type of object. The present inventors are currently concerned with the particular problem of generating a surface model of the dentition of human patients. Such models are useful in planning orthodontic treatment using a computer, among other things. FIG. 8 shows a complete 3D model of the upper arch 130, including teeth 132, of a human as it might be displayed on a monitor of a general-purpose computer, after in-vivo scanning of the arch with a scanner of the type shown in FIG. 1. The scanning is used to create a cloud of points representing the teeth and associated anatomical structure. The cloud of points is initially represented as a large number of individual frames, which are registered to each other using a cumulative registration procedure. The methods of the present invention take the resulting cloud of points from the cumulative registration model (a noisy and inhomogeneous set of scan data) and create a single 3D surface model. This single 3D surface model is shown in FIG. 8. The modeling software includes user interface tools that allow the user to display the 3D surface model as either a continuous surface without showing the edges of the triangles (as shown in FIG. 8), or as a "wire frame model" in which the edges of the triangles are displayed. An example of the "wire frame model" is shown in FIG. 9.

Figure 9:
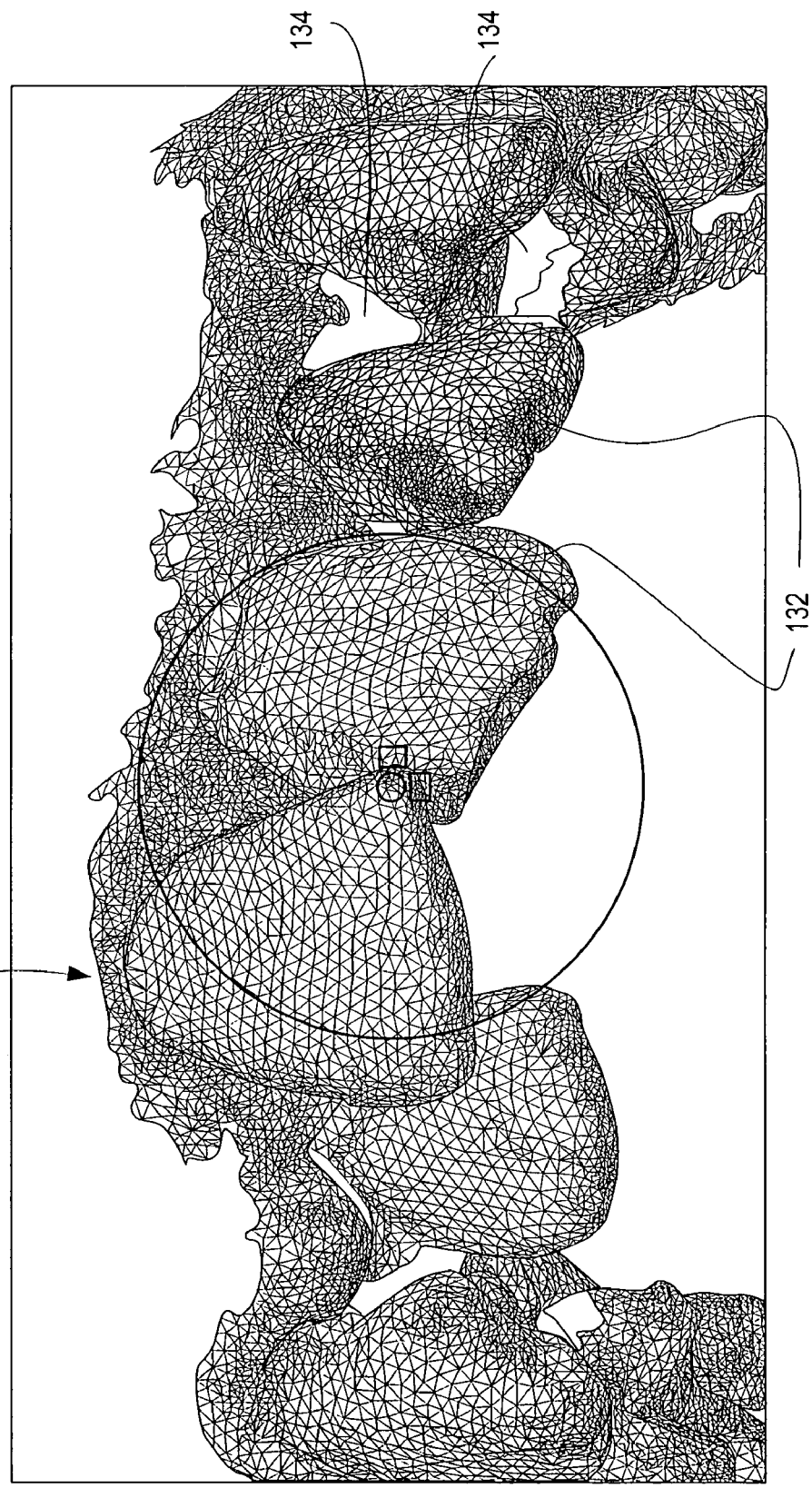
FIG. 9 shows the three-dimensional surface of FIG. 8, but this time showing a "wire-frame" model in which the edges of the triangles are indicated on the display.

The surface model may include holes or gaps in scan data, indicated at 134 in FIG. 9. These gaps are not closed by triangle surfaces since the edges of any triangles closing the gaps would exceed distance criteria for triangle edges. Hence, the gaps are either ignored or else filled in using other techniques, such by use of virtual models of teeth or otherwise. The PCT application of OraMetrix, publication no. WO 01/80761, describes several methods for closing gaps in scan data and the interested reader is referred to that document for further details on closing gaps. Additionally, the entire model may include discrete portions that are not connected to each other. For example, if the scan data is rather poor, the majority of the arch is represented as a single continuous surface and a portion of one tooth may "float" in space in the correct position. In this situation, the procedures described herein would be applied to both the point cloud representing the arch and to the point cloud representing the portion of the tooth that "floats" in position next to the point cloud of the arch.

Figure 10:
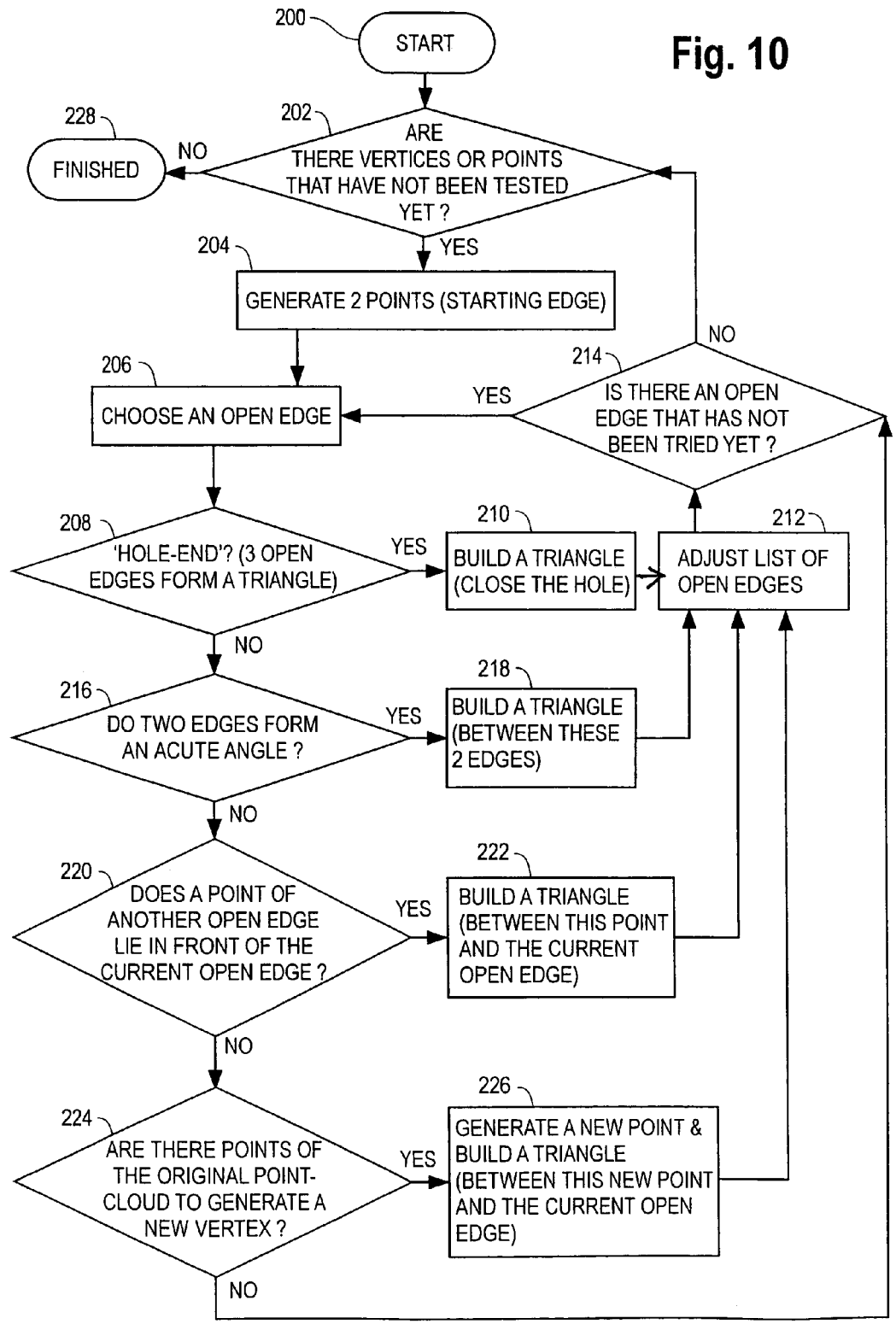
FIG. 10 is a flow chart showing a preferred sequence of software operations on a point cloud to construct a single surface from a point cloud.

FIG. 10 is a flow chart showing the execution of software instructions that create a single surface from a point cloud in one embodiment. At the start of the procedure (200), a point cloud is stored in memory. A list of points is initialized to all the points in the point cloud. Each point consists of three-dimensional coordinates. Each point is assigned an index number. The list of open edges is empty (no entries), the list of closed edges is likewise empty, and the list of triangles forming the surface is also empty.

At the first step 202, a check is made to see if there are vertices or points that have not been tested for formation of a triangle. At the beginning of the procedure, the answer of course is yes, so the process proceeds to step 204. At step 204, the process needs to generate two starting points which creates the initial open edge. This was described above in conjunction with FIG. 4A. The first and second points are generated and the open edge between the points is added to the list of open edges. The process proceeds to step 206. The process selects an open edge. At the beginning, there is only one open edge (newly created from the first two points). The process then proceeds to blocks 208, 216, 220, 224, which describe rules for generating triangles from open edges. The first rule is the test in block 208. This test asks if the open edge is a boundary of a "hole", i.e., is the open edge one of the three open edges that together form a triangle. If so, the processing reverts to block 210. A triangle is formed that closes this hole, and the list of triangles is updated. The process proceeds to block 212, where the list of open edges is adjusted to remove the open edge selected in block 206 and the other two open edges the formed the "hole".

In the case of the first open edge, of course block 208 will be answered in the negative, so the process reverts to block 216. Here, a test is made to see if the open edge selected at block 206 and tested at block 216 is adjacent to another open edge (share a common vertex) and if the angle between the edges is an acute angle. If so, the processing reverts to block 218 and a triangle is formed between these two edges (see FIG. 7, formation of triangle 112), the list of triangles is updated, and the process reverts back to process 212 and the list of open edges is adjusted accordingly.

Again, in the case of the initial or first open edge, block 220 will be answered in the negative, and so the process reverts to block 224. Here, a test is made to see if there are points in the point cloud to generate a new vertex. The block 224 is described below in conjunction with FIG. 10A. If so (and this will ordinarily be the case at the beginning of the procedure), the process proceeds to block 226. At this block, a new point is generated using the weighted average procedure described above, see FIGS. 4A, 4B and 6, and a new triangle is constructed from the new vertex and the open edge selected at block 206. The points list is then updated, in that the points used in the weighting process to form the new vertex are marked as having been used and are not used in further modeling. The processing proceeds to block 212, where the list of open edges is adjusted to add the two new open edges created by the new triangle. If, at block 224, there are no further points in the point cloud to generate a new vertex adjacent to the open edge in question, the process reverts back to step 214, where a test is conducted to see if there are other open edges that have not been tried by processing through the modules 208, 216, 220 and 224. If block 220 is answered in the positive, then the process proceeds to the block 222 where a triangle is built between this point and the current open edge and the process reverts to the block 212.

As is shown in FIG. 10, after the open edge has been processed by modules 208, 216, 220 and 224 and the process has succeeded in generation of a new triangle and the open edge list is adjusted at module 212, the process continues to module 214. At this module, the software asks whether there are any open edges that have not been tested by the modules 208, 216, 220 and 224. If untested open edges exist, the processing reverts back to step 206, a new open edge is selected, and the process of applying modules 208, 216, 220 and 224 to the new open edge is repeated.

If, at module 214, there are no untested open edges remaining, the process reverts to step 202 to see if there are points in the point cloud that have not been tested. If there are points in the points list that have not been tested, a new starting edge is selected in a new part of the point cloud (as indicated at step 204) and the processing of FIG. 10 repeats for the new region in the point cloud (for example, where there are "floating" regions). On the other hand, if the answer is negative at step 202, then the process is finished at the block 228.

The module 224 of FIG. 10 will now be described in further detail in conjunction with FIGS. 10A–10E. The goal of module 224 is to determine whether there are points in the original point cloud to generate the new vertex in the surface. This module 224 is where the selection of points in the point cloud occurs and the weighting algorithm is applied to select the new vertex, and where the new vertex is tested against rejection criteria. These procedures insure that the triangle surface matches the point cloud with a minimum of deviation.

Figure 10A:
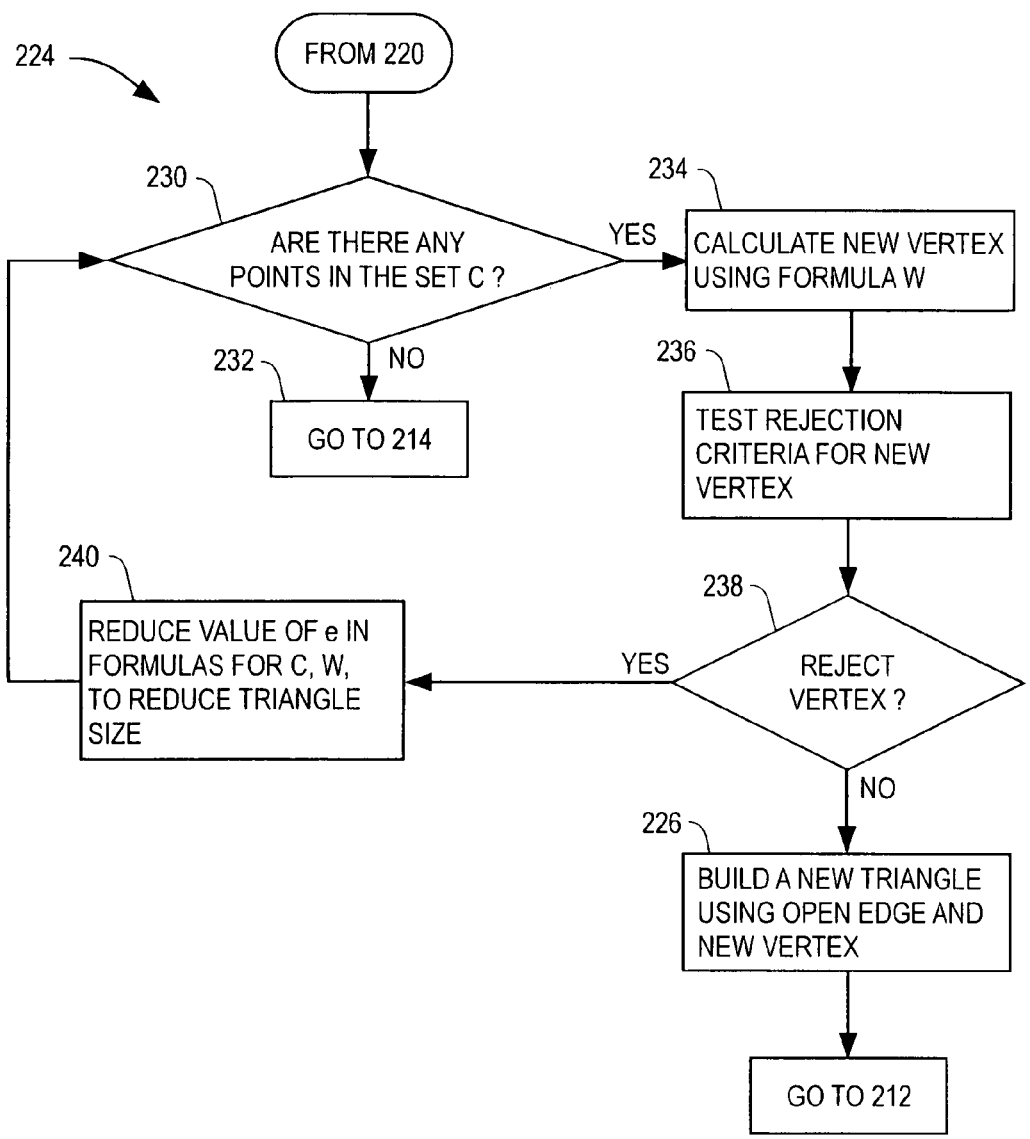
FIG. 10A is a more detailed flow chart for step 224 and 226 of FIG. 10.

Referring now in particular to FIG. 10A, the processing of module 224 proceeds with a block 230 which determine whether there are points in the point cloud which are members of a set C. Set C is determined as follows.

Let P1, P2 be the vertices of the open edge, $\vec{n}$ the normal-vector of the existing triangle adjacent to the edge P1, P2. Then let $e = \|P_2 - P_1\|$, the length of the open edge.

C is expressed as follows:

$C = \{P | \|P-P_1\| < 2e \hat{} \|P-P_2\| < 2e \hat{} (P_2-P_1) \times (P-P_1) > 0\}$,
which is the set of all points, which are not too far away from the two vertices of the open edge, and do not lie 'behind' the open edge. Then the new vertex V will be given formula W:

$$W: V = \frac{\sum_{P \in C} P \cdot w_{P,P_1} \cdot w_{P,P_2}}{\sum_{P \in C} w_{P,P_1} \cdot w_{P,P_2}}$$

with the weights $w_{P,P_i} = e^2 - (e - \|P - P_i\|)^2$

These weights are >0 for every P∈C and have their maximum along the half-circle of points, which form equilateral triangles with P1 and P2. The weighting of points and selection of points in set C insures that the mesh tends to be quite regular.

Figure 10B:
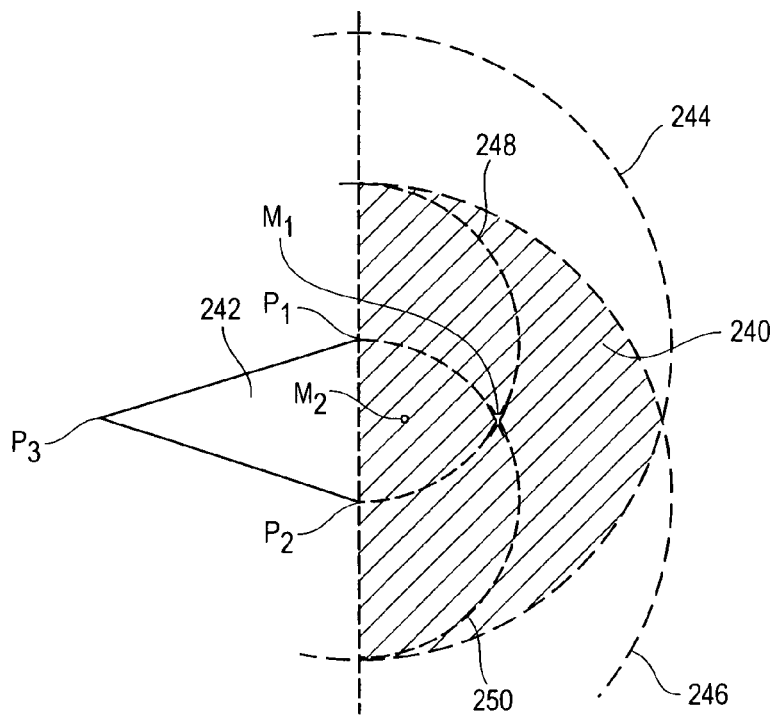
FIG. 10B illustrate selection criteria for selecting a set of points used to generate a new vertex in the single mesh surface.

FIG. 10B shows the exiting triangle consisting of points P1, P2 and P3. The line connecting P1 and P2 is the open edge, the hatched area 240 corresponds to the set C. The points in set C are delimited to the left by the plane passing through the points P1 and P2 and perpendicular to the plane containing the triangle 242; points in set C are also delimited to the right by the two half-spheres 244 and 246 with center P1 and P2, respectively, and having a radius of 2e. The point M1 shows, where the weights have their maximum. If the new vertex selected from the hatched region 240 does not satisfy the rejection criteria test in module 236 (FIG. 10A)

described below, the value of e is reduced in the formulas for C and W, indicated at step 240 in FIG. 10A. The new area is indicated by the smaller half spheres 248 and 250, with point M2 being the location where the weights are a maximum.

Referring again to block 230 of FIG. 10A, if there are no points in the set C, the processing reverts back to block 214 as indicated at 232.

If there are points in the point cloud in the set C, the process proceeds to step 234 and the calculation of the new vertex using the formula W above.

At step 236, the new vertex is tested against rejection criteria for a new vertex. There are two criteria that are used in the preferred embodiment, however it is possible to just use the second criterion alone:

1: The variation of the surface normals of the source data points in the set C used to construct the vertex must be less than a threshold value; and 2. The angle between the surface normals of the adjacent triangle and the new triangle must be less than a threshold value.

Figure 10C:
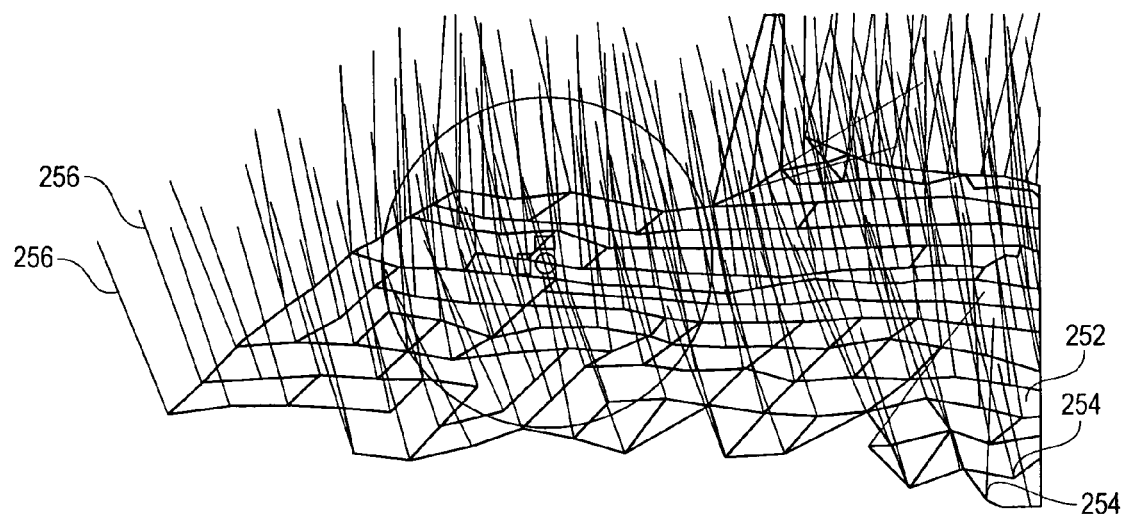
FIG. 10C–10E illustrates rejection criteria used to evaluate whether a vertex constructed according to the weighting of points selected in accordance with FIG. 10B is accepted; the rejection criteria insures that new vertices are selected which minimize surface deviation in the triangle surface from the point cloud source data.
Figure 10D:
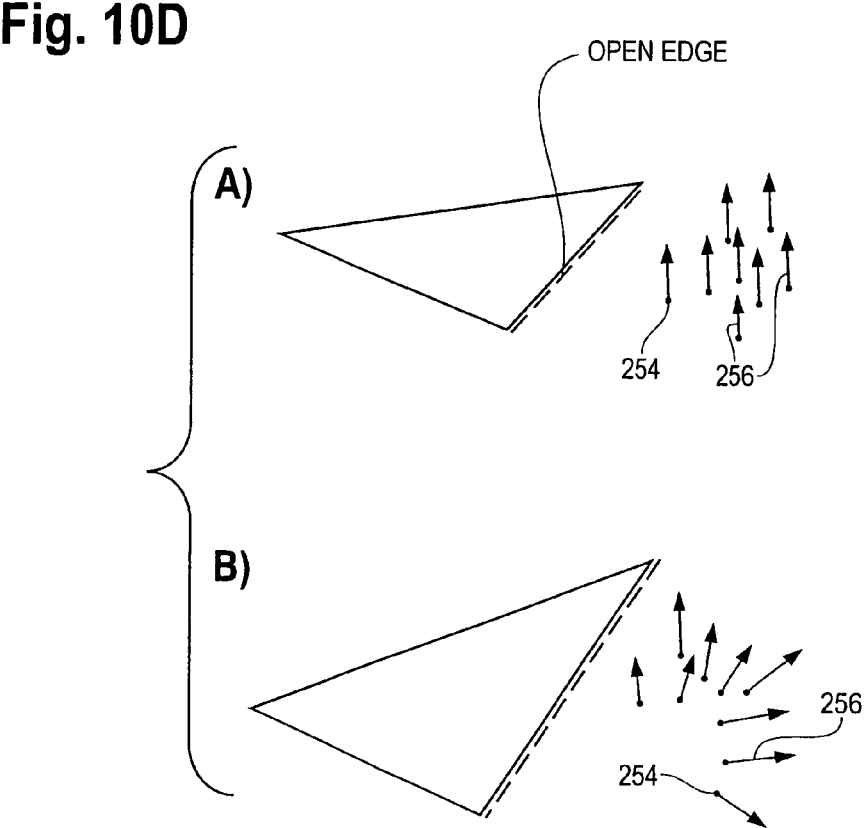

The first criterion will be explained in conjunction with FIGS. 10C and 10D. Each point in the point cloud has a surface normal, defined as a vector extending from the point in a direction normal to a weighted average of the triangle surfaces containing the point (the triangles here are triangles constructed from the source data, not in the single mesh surface). Within each frame of data forming the cloud, the data points are triangulated in a way such that points, which are next to each other in the frame, are connected by a triangle, An example of this is shown in FIG. 10C. The points 254 in the individual frame form a surface 252. The lines 256 extending from the points 254 are a weighted average of the normal vectors (not shown) of the adjacent triangles that include each point. FIG. 10D, part A, shows a situation where the surface normal vectors 256 of the points 254 in the set C are all relatively closely aligned. This indicates that there is relatively little surface curvature. If the variation in the surface normal vectors 256 is less than a threshold, the vertex selected from the set of points 254 passes the first criteria. FIG. 10D, part B, shows the situation where there is a large degree of variation in the surface normal vectors, indicating a large degree of curvature in the surface. In this situation, the vertex selected from the points in FIG. 10D, part B, would be rejected.

Figure 10E:
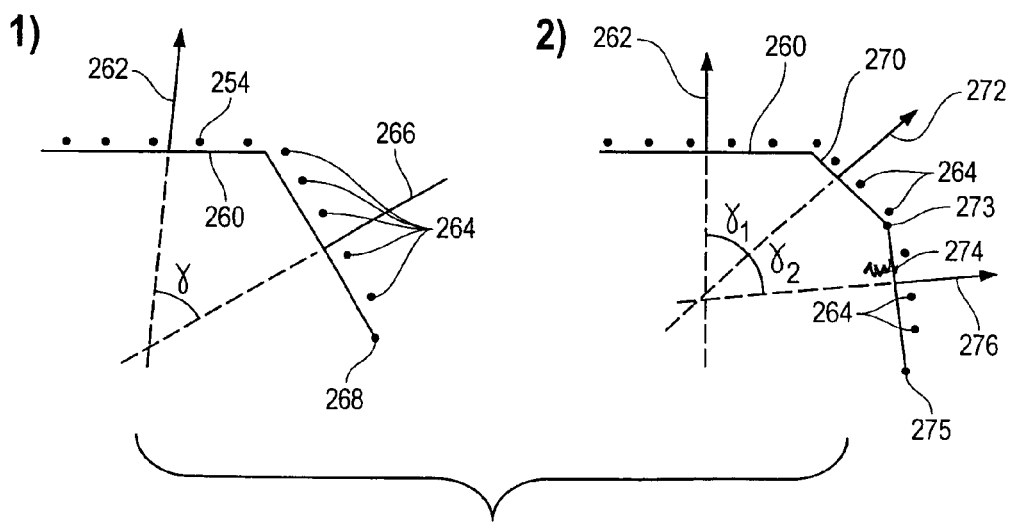

The second criteria in FIG. 10A, block 236, is a test of the angle between the existing triangle having the open edge and the new triangle constructed between the open edge and the newly selected vertex. This angle must be less than a threshold value in order for the vertex to satisfy the selection criteria. As shown in FIG. 10E, part 1, an exiting triangle (shown on edge) has open edge 260, wherein the source data points 254 indicate little surface curvature. The triangle has a surface normal vector 262. If the source data points 264 are used to construct a new triangle, the triangle would have a new vertex 268 and a surface normal vector 266. The angle γ between the triangles is greater than the threshold and thus vertex 268 will be rejected. The processing of FIG. 10A indicates a rejection at 238 and the processing proceeds to block 240, where the value of ε in the equations for C and W are reduced. The process looks at points closer to the open edge and results in a selection of a new vertex 273, forming a triangle with edge 270 and new surface normal 272 having an angle γ1 relative to the vector 262 as shown in FIG. 10E. The angle γ1 is less than the threshold so the new vertex 273 is accepted. Further processing results in a new vertex 275 being selected forming a triangle with edge 274, in which the angle γ2 between the new surface normal 276 and the normal vector 272 is also less than the threshold. Thus, the process shown in FIGS. 10D and 10E insure that the new vertex is chosen that minimizes deviation from the point cloud, and more specifically corresponds to the localized curvature represented by the points 264.

From the above description, and with reference to the previous Figures, it will be appreciated that we have described a method for creating a surface representation of a three-dimensional object. The method includes the step of scanning the object with a scanner and storing scan data in a memory of a computer, as shown in FIG. 1. The scan data comprises a cloud of points 30, each point having three-dimensional spatial coordinates. The method includes the step of constructing within the computer an initial triangle derived from points in the scan data. See FIGS. 4A–4B and the previous discussion. The method continues with the step of repeatedly constructing within the computer adjacent triangles (see FIGS. 4C–4G and 5–7), the adjacent triangles having at least one common edge with a previously constructed triangle. The adjacent triangles have vertices comprising either the points forming said initial triangle (FIG. 4B) or points constructed from a weighted averaged of points in the scan data in the region of the vertices and in which predetermined rules or criteria for selection of vertices are obeyed. (See FIGS. 4B–4G, 10A–10E) The surface representation comprises the initial triangle and the adjacent triangles.

In still another aspect, a method has been described for creating a surface representation of a three-dimensional object from a cloud of points, each point having three-dimensional spatial coordinates. The method comprises the steps of storing the cloud of points in a memory of a computer and storing, in the memory of the computer, a list of points comprising the cloud of points and a list of open edges. The method further comprises the step of providing machine executable instructions for the computer that operate on the cloud of points, the instructions:

1) constructing an initial open edge from points in the cloud of points (FIG. 4A, edge 44);

2) constructing a triangle forming a portion of the surface representation from the open edge using predetermined rules for generating triangles forming the surface representation (FIG. 4B, forming triangle 1 using point 48 and initial points 40 and 42, steps 224 and 225 of FIG. 10);

3) adjusting the list of open edges in view of the construction of the triangle (step 212, FIG. 10);

4) checking to see if there are open edges that have not been tried yet to form a triangle forming a portion of the surface representation, and if so, repeating steps 2) and 3) (step 214, FIG. 10 and the previous discussion of FIG. 10 and FIGS. 4A–4G);

5) as steps 2), 3) and 4) execute, adjusting the list of points by marking the points in the list of points that are used to generate vertices of triangles in step 2) and not using them further in the modeling procedure (indicated by the voids in the clouds of points in FIGS. 4B–4G); and 6) repeatedly iterating steps 2), 3), 4) and 5) until the instructions have attempted to generate triangles from all open edges in accordance with the predetermined rules for generating triangles (rules 208, 216, 220 of FIG. 10), and the instructions have attempted to generate a vertex of a new triangle from all remaining points in the list of points in accordance within predetermined rule(s) for generating vertices of triangles forming the surface (step 224, FIG. 10).

It will also be appreciated that we have described a method for constructing a three-dimensional model of an anatomical structure (such as teeth or any other anatomical structure), comprising the steps of:

scanning the anatomical structure with a scanner and obtaining scan data (see FIG. 1);

converting the scan data to a cloud of points (described in the prior PCT application of OraMetrix or generally known in the art of 3D scanners);

storing the cloud of points in a memory of a computer (FIG. 1); and executing machine executable instructions in the computer, the instructions operating on the cloud of points to construct an initial triangle (FIG. 4A) and a multitude of adjacent triangles (FIGS. 4B–4G) forming a single continuous surface representing the object, the triangles comprising planar surfaces having three vertices, wherein the vertices comprise points forming the initial triangle and points computed as a weighted average of nearby points in the cloud of points.

Crown Detection Process

Figure 11:
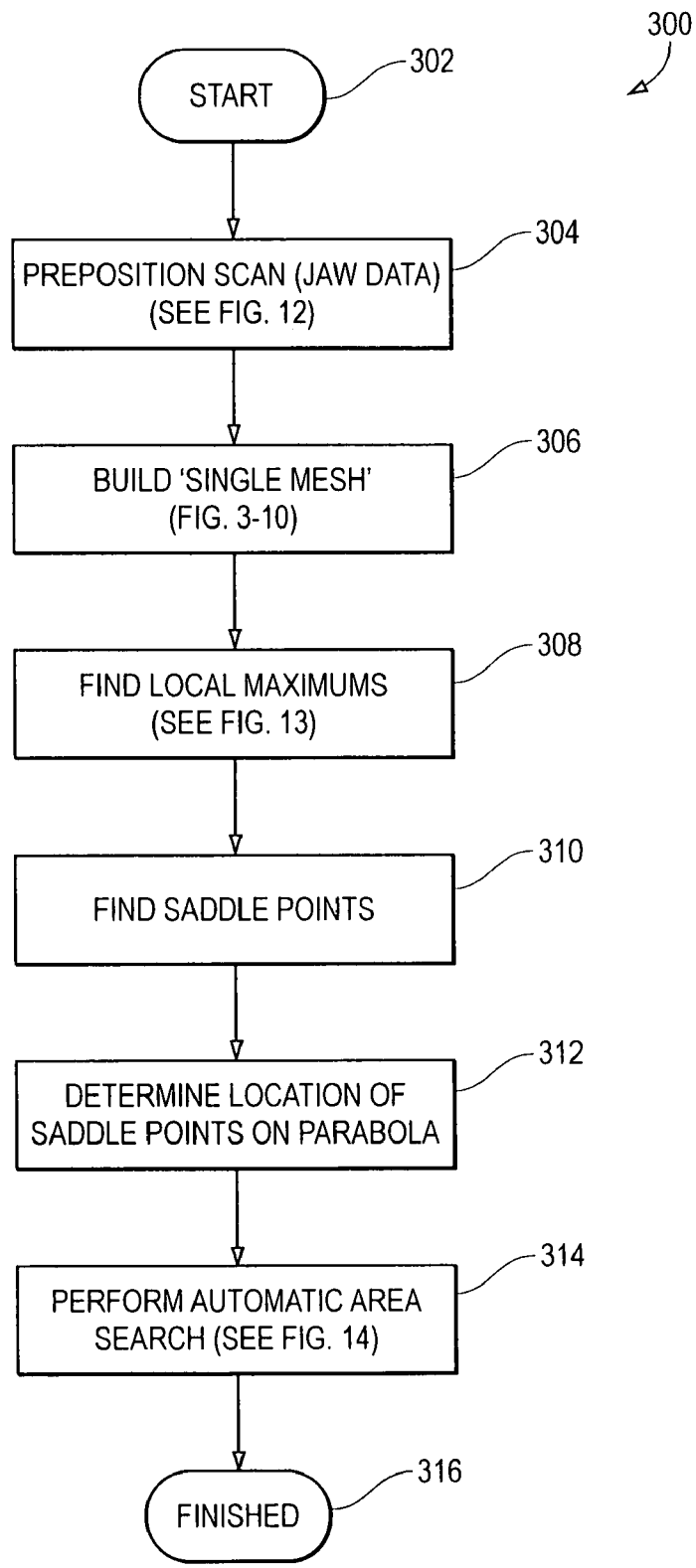
FIG. 11 is a flow chart showing a process executed in software by the computer of FIG. 1 for automatically identifying crowns and gingival tissue from a virtual model of teeth and associated structure. The virtual model is preferably a three-dimensional single mesh surface, such as one developed in accordance with the procedures of FIGS. 4–10E.

Referring now to FIG. 11, an overall process 300 of crown (and gingival tissue) detection is shown in flow chart form in FIG. 11, which will now be described. The aim of the procedure 300 is to analyze the virtual model data and to determine which portions of the data match the gums and which portions correspond to teeth. Thus, both the transitions between the teeth and the gums and those between adjoining teeth need to be detected, and the portions between these transitions need to be correctly assigned to the corresponding portions of the scanned jaw.

Figure 12:
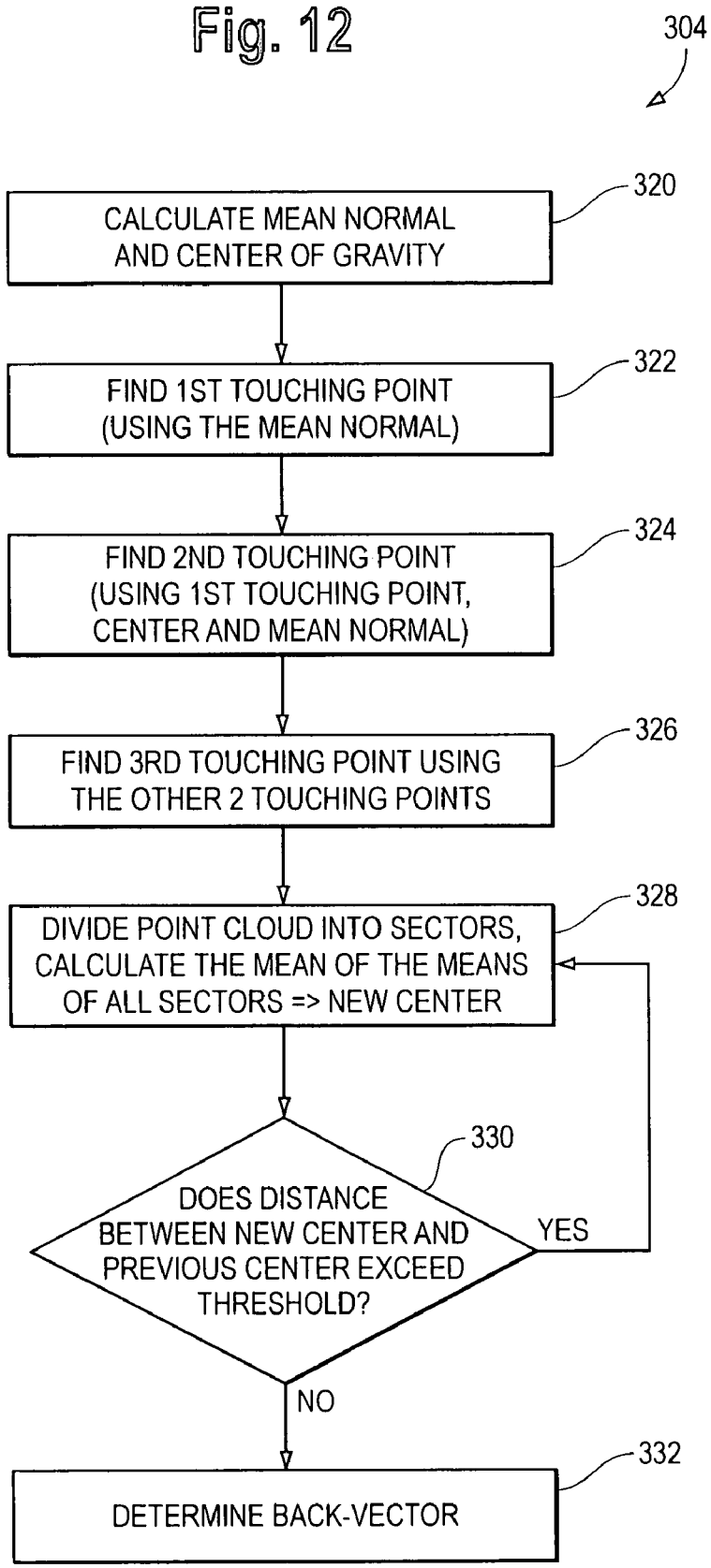
FIG. 12 is a flow chart of a process executed in software for positioning the virtual model relative to a plane.

At step 302, the procedure is started. The first step shown in FIG. 11 is a step 304 of pre-positioning the scan data relative to a plane. This process is shown in FIG. 12 and described more in detail below. The next step shown is building a single mesh surface 306. At the start 302 of the procedure of FIG. 11, the procedure assumes that three-dimensional virtual model of the dentition and gingival tissue has been obtained by some process (e.g., scanned) and that the virtual model is stored in the memory of the computer. In the case where the virtual model is an inhomogenous point cloud with noisy data, the process includes the step 306 of constructing the single mesh surface, described above in detail. In the event that the virtual model is a continuous, well-defined surface (and preferably a single surface), step 306 may be omitted. Also, the order of steps 304 and 306 can be changed since the step 304 of pre-positioning the virtual model could be done in any form of the scan data, point cloud, mesh or otherwise.

Figure 13:
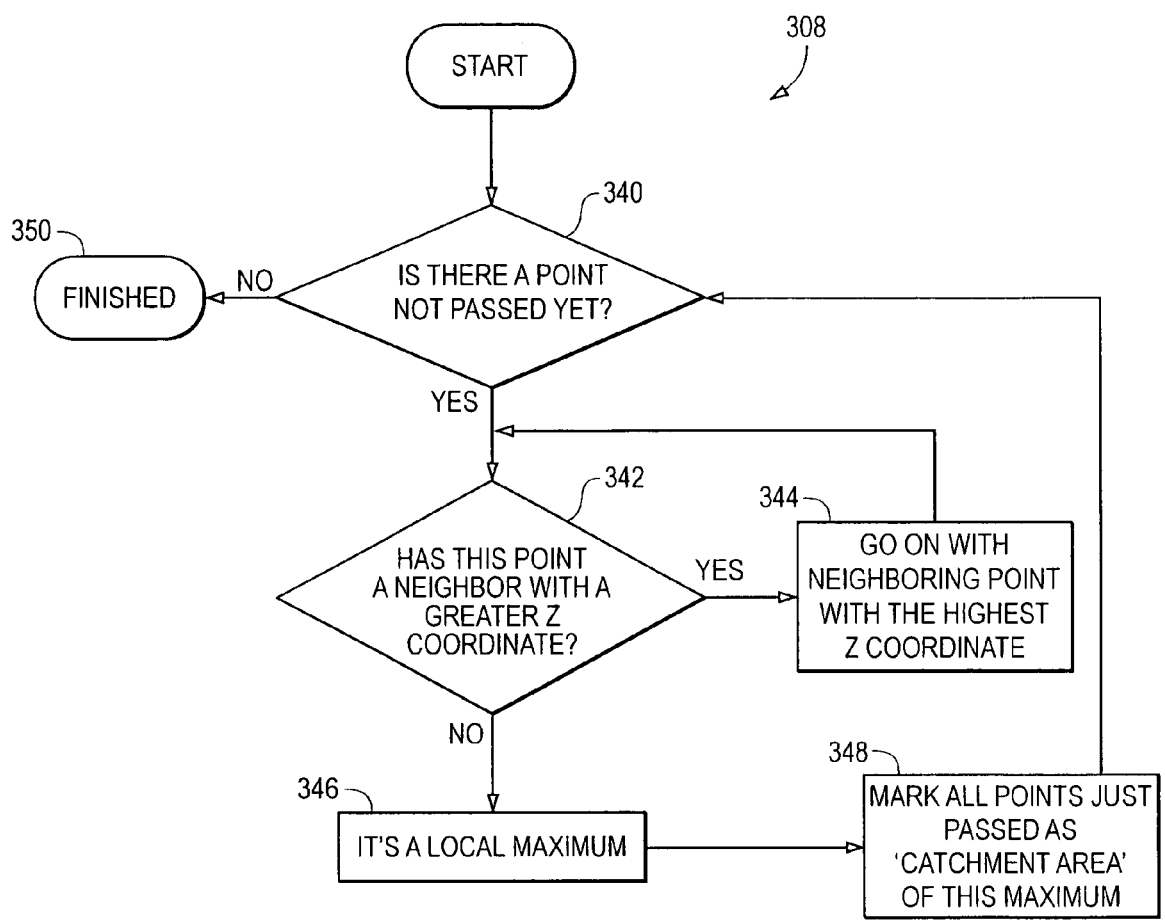
FIG. 13 is a flow chart of a process executed in software for finding local maxima in a virtual model, and associated areas bounded by the local maxima ("catchment areas" herein).

The process continues with a step 308 of finding the local maxima in the model and the areas defined by the local maxima, "catchment areas" as defined herein. This procedure is illustrated in FIG. 13 and described at length below. The local maxima are the cusps or high points of the teeth. A given tooth may have more than one maxima.

Figure 14:
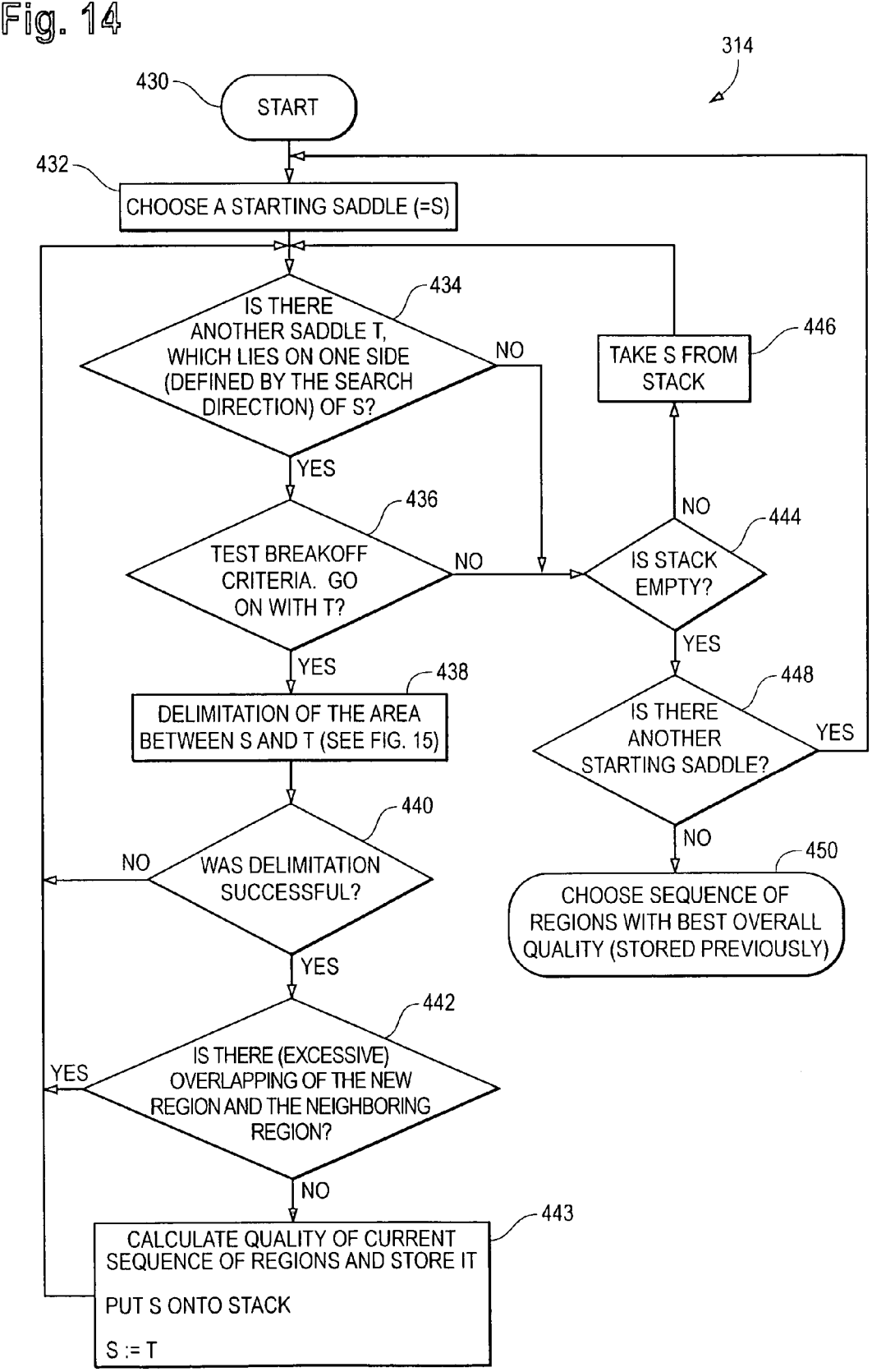
FIG. 14 is a flow chart of a process executed in software for an automatic area search, the process of FIG. 16 used for grouping areas which together form a tooth crown.

The processing continues with a step 310 of determining the location of saddle points in the virtual model and a step 312 of determining the position of the saddle points along a dental arch form, which makes use in one embodiment of a parabolic coordinate transform. The order in which steps 310 and 312 execute are interchangeable, as will be understood from the following description. The processing continues with a step 314 of performing an automatic area search. This procedure is shown in FIG. 14, and invokes sub-routines shown in FIGS. 15 and 16. Subsequently, the process is finished at step 316. The result of the process is an identification in the model of the tooth crowns, and associated gingival tissue, the primary objective of the present invention. The processes shown in FIG. 11 will now be described in detail in the following sections.

Figure 17:
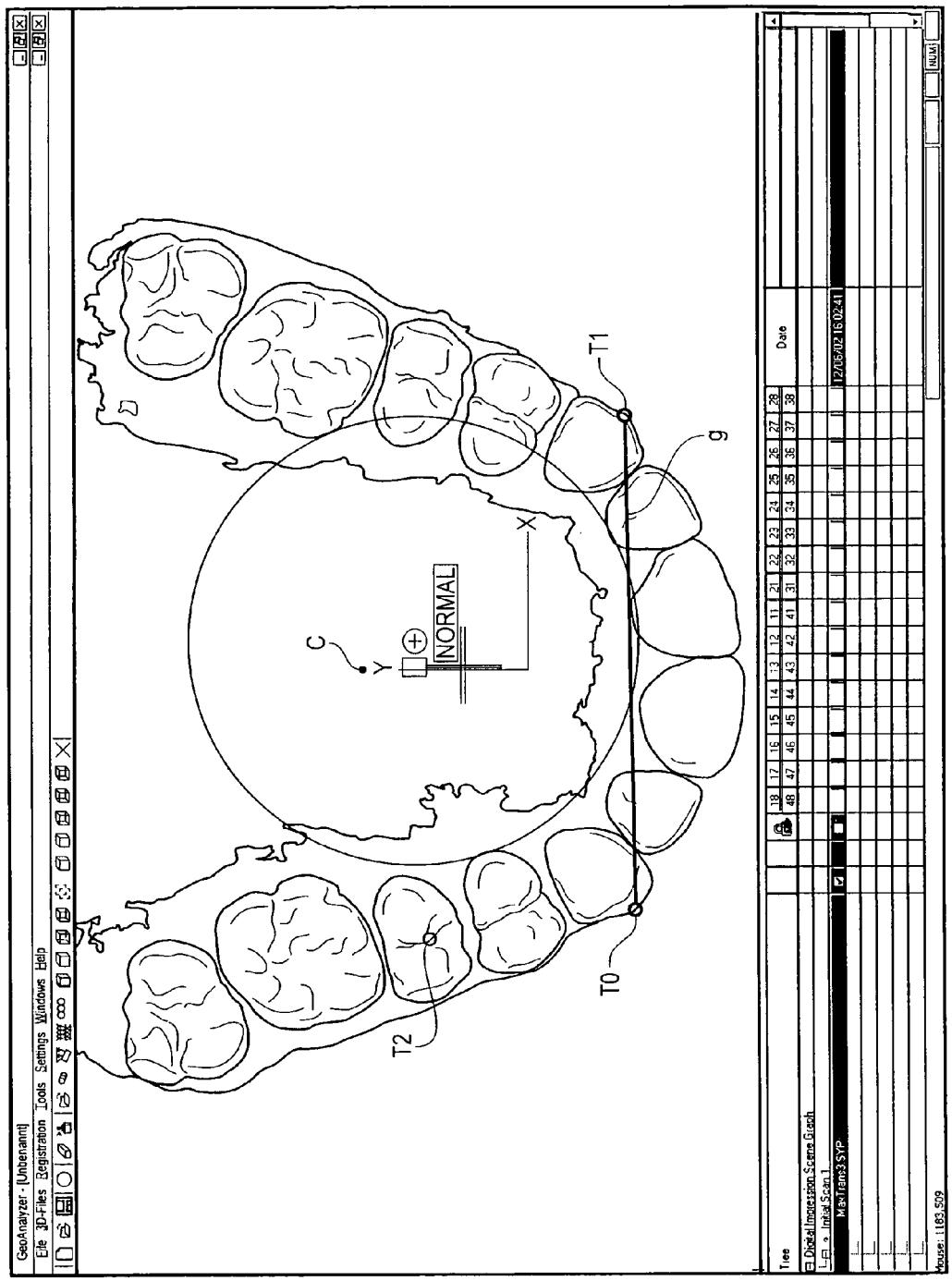
FIG. 17 is a screen shot from the computer of FIG. 1 showing a virtual model of the dentition and gingival tissue, showing the identification of points T0, T1, and T2 of a plane used to orient the model in accordance with the process 304 of FIGS. 11 and 12.

Pre-Positioning Model (Step 304) (FIGS. 12, 17)

The aim of this procedure 304 is to perform a transformation $T_V$ which spatially positions the cloud of points (or single mesh surface or other form in which the data is represented) in such a manner that the plane of occlusion approximately corresponds to the plane of the x-y coordinates, the "center of gravity" of the of the arch is near the z coordinate axis and the opening of the palatomaxillary arch is pointing in the direction of the positive y coordinate.

In the event that the procedure 304 executes on a cloud of points, the procedure can be sped up by only using a subset of the cloud of points, e.g., only every $10^{th}$ point. This positioning algorithm is quite robust, so it does not matter whether one uses the original point cloud or the single mesh surface. If one uses the original point cloud, and only a subset of points is used, the choice of points has no influence on later steps in the process 300. The algorithm can handle any number of points, from a single mesh with some 10 thousand points to a very dense scan with several million points. In the event that the point cloud is used, a numerical index assigned to each point is used for the point selection, i.e., for the subset of points to use. All the points in the point cloud are consecutively numbered, and the method uses every point with an index divisible by 10, for example.

In a first step 320 in process 304, a first approximation of an up vector and center point is made. The up vector is the mean of the normals of all vertices, which gives a rough approximation of the up vector (the vector that is transformed into the positive z coordinate by $T_V$). The mean of all X, Y, Z coordinates of all points in the model forms the first rough approximation of the center point C ("center of gravity" of the arch).

Thus, the center point C and the up vector can be represented by the equations:

Center point:

$$C = \frac{\sum P_i}{\|\sum P_i\|},$$

where $P_i$ are the data points.

Up vector:

$$\vec{u} = \frac{\sum \vec{n_i}}{\|\sum \vec{n_i}\|},$$

where $n_i$ are the surface-normal-vectors of the data-points The process continues with determining a plane in which the arch is oriented to. It is not necessary to arrive at a specific plane. In the present example, an approximation of a plane of occlusion $E_O$ is determined. Reference is made to FIG. 17 in the following discussion. This process includes sub-steps 322, 324 and 326 in FIG. 12. In this process, a plane is "placed" approximately on three points of contact of the jaws. Processes 322, 324 and 326 are processes for finding the three points. At step 322, the highest point in relation to the up vector forms the first point of contact $T_0$. At step 324, the second point of contact $T_1$ is formed by a plane touching $T_0$ and perpendicular to the up vector and tilted towards the center point. $T_1$ is the first point beyond the center (seen from $T_0$) which this plane touches. A straight line g is drawn through $T_0$ and $T_1$. At step 326, starting from the straight line g, another plane is tilted toward the center C (or in both directions if g is situated near the center) until $T_2$, the third point of contact, is formed.

Equations used to find T0, T1 are as follows.

$$T_0 = P_m, \text{ with } \forall i \neq m: P_i \cdot \vec{u} \leq P_m \cdot \vec{u}$$

$$T_1 = P_n, \text{ with}$$

$$n \in J = \{j | P_j \cdot ((\vec{u} \times (C - T_0)) \times \vec{u}) \geq C \cdot ((\vec{u} \times (C - T_0)) \times \vec{u})\}$$

and with $$\forall i \in J,$$

$$i \neq n: \frac{\vec{u} \cdot ((P_i - T_0) \times (\vec{u} \times (C - T_0)))}{\|(P_i - T_0) \times (\vec{u} \times (C - T_0))\|} \leq \frac{\vec{u} \cdot ((P_n - T_0) \times (\vec{u} \times (C - T_0)))}{\|(P_i - T_0) \times (\vec{u} \times (C - T_0))\|}$$

where x is the vector cross product operator and · indicates scalar multiplication.

The formula for T2 is rather complicated to express in mathematical terms, because there are different cases, depending on the constellation of C, T0 and T1. However, persons skilled in art will be able to develop algorithms to find T2 from the present discussion, or find some other point in which to construct a plane containing T0 and T1 for the present purposes of orientation.

The plane defined by $T_0$, $T_1$, and $T_2$ forms the plane $E_O$ that is sought (approximation of the plane of occlusion).

To reduce sensitivity to excessive noise or artifacts, is preferable not to take the first point found for T0, T1 and T2, but rather the n-th point should be selected (n>0). By this we mean that we do not, as written in the formulas above, take the maximum value of a set, but we sort the values and take the n-th value, for example the 10th (i.e. we take a point, so that there are exactly nine other points, which would more fulfill our criterion.). We do this for T0, T1 and T2. In fact this point is one of the main reasons for the robustness of this process step.

The process continues with step 328 of refining or more precisely determining the location of the center of the arch. The problem, particularly when a point cloud is used in procedure 304, is that there can be considerable variation in the local point density in different parts of the scan. Therefore the mean X, Y, Z value of the points does not generally lie in the center of the virtual model. The procedure in step 328 resolves the location of the center so that the center does not depend on an inhomogeneous point cloud density.

At step 328, all points of the cloud of points not exceeding a certain distance (e.g., 8.0 mm) from $E_O$ are projected onto $E_O$. Starting from the existing center point, the x-y plane is divided into sectors of the same angle into which these points are sorted. The center of gravity of the centers of gravity of the points in each sector is the new center. At step 330, the distance between the new center and the previous center is determined and a comparison is made to a threshold. If the distance is greater than the threshold, the process loops back to step 328 and the process repeats. This gives a better approximation of the center point. Repeated iteration of steps 328 and 330 yields the center.

The projection used in step 328 is as follows:

$$p: R^3 \rightarrow R^2$$

$$(P_x, P_y, P_z) \mapsto (P_x, P_y)$$

The sectors $S_i, i \in \{0, \ldots, 99\}$ are used.

The point P belongs to the sector $S_n$ with:

$$n = \left\lfloor \arctan(P_x - C_x, P_y - C_y) \cdot \frac{100}{2\pi} \right\rfloor,$$

where arctan (x,y) is similar to arctan (y/x), but within the right quadrant, regarding the signs of both x and y.

In the repeated iterations of step 330 and 328, the result of one iteration is a new approximation of the "center of gravity" C, which can than be used (in the above formula) for the next iteration. We can stop this process either after a fixed number of iterations (e.g. 5) or when C does not change significantly (e.g. 1.0 mm) any more.

The positioning process 304 has a final step 334 of determining a back vector that lies on the plane of occlusion and points toward the opening of the palatomaxillary arch. If a unit vector is formed from the center toward the center of each of the sectors of c) in which a minimum number of points has been sorted and if their mean value is formed, the front vector is obtained (=−back vector).

The front vector is represented by the following equation:

Front vector $$\vec{f} = \sum_{j \in J} \left( \sin\left(\frac{j \cdot 2\pi}{100}\right), \cos\left(\frac{j \cdot 2\pi}{100}\right) \right), \text{ with}$$

$$J = \{j \in \{0, \ldots, 99\}, |S_j| \geq 8\}, \text{ where } |S_j|$$

where $|S_j|$ is the number of points which belong to sector $S_j$.

Back-vector: $\vec{b} = -\vec{f}$.

Referring now to FIG. 11 again, the process proceeds to the next step 306 of construction of a single mesh surface, in the event that the procedure of FIG. 11 is started with a point cloud representation. If a single mesh was used initially, the step 306 is not needed. If step 306 needs to be performed, the process described previously in conjunction with FIGS. 2–10E executes. The result of step 306 is the storage of a single mesh virtual model of the dentition and gums as a continuous surface. The problem at hand is to separate the virtual crowns of the teeth from the virtual gingival tissue. To do this, the processes 308, 310, 312 and 314 execute, as explained in the following discussion.

Figure 18:
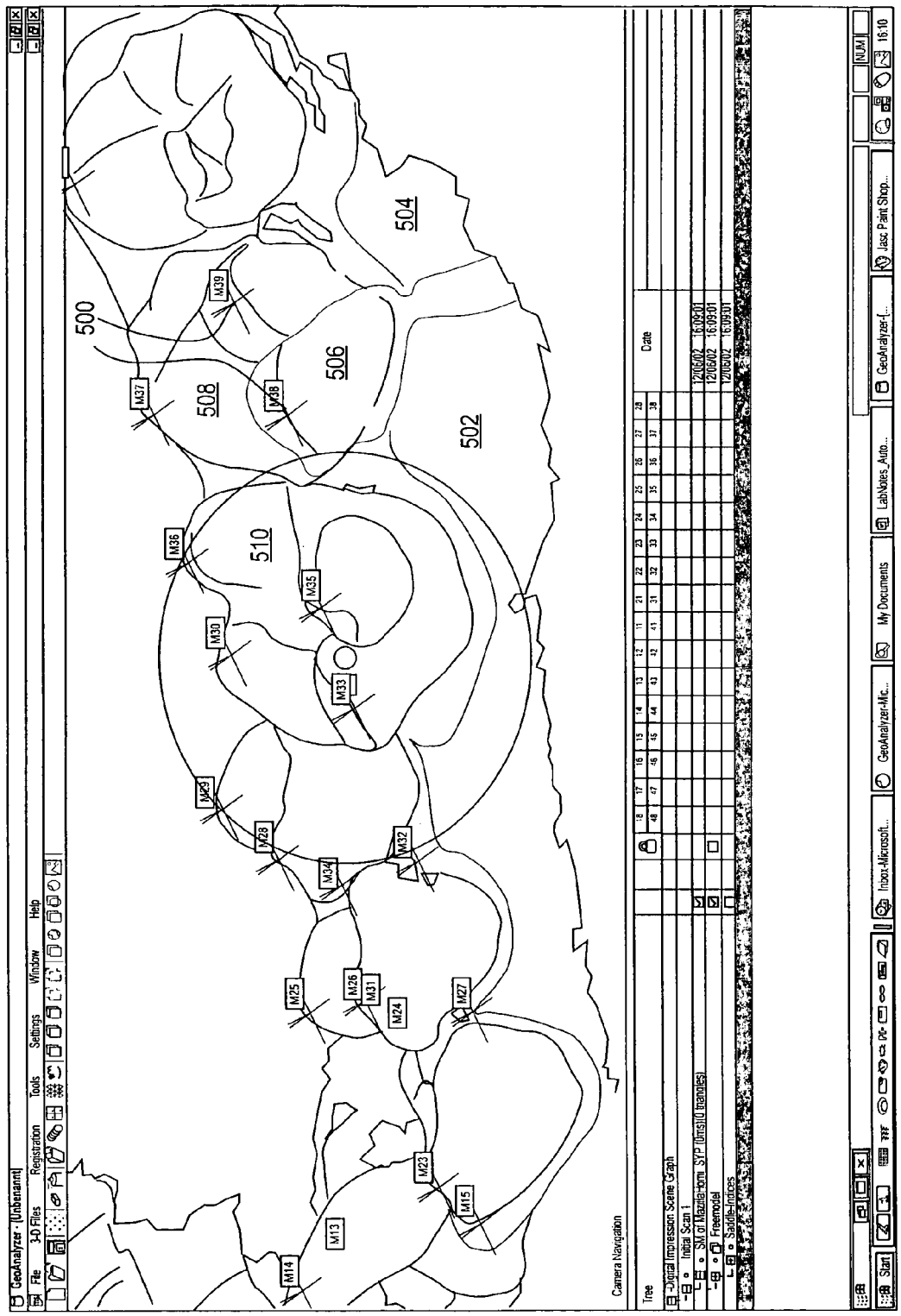
FIG. 18 is a screen shot showing the virtual model showing the local maxima and "catchment areas" identified from the operation of the process 308 of FIGS. 11 and 13.

Find Local Maximums and Their Catchment Areas (Process 308)(FIGS. 13 and 18)

We now have a single mesh consisting of adjacent triangle surfaces, which is oriented in such a way that the plane of occlusion $E_O$ is "above", i.e., pointing toward the positive z direction. The neighborhood relationship of points is also defined through triangulation: Two points neighbor each other if there is a triangle which references the two points. In the strict sense, each point that has no neighbor with a greater z coordinate is a local maximum.

In the process 308, if, starting from any point, one keeps going to the neighboring point with the greatest z coordinate until this is no longer possible, one finds a maximum M. The point of origin then belongs to the catchment area of M. If this procedure is repeated for all points, one obtains all maximums and their catchment areas.

However, since this strict definition of a maximum leads to very many maximums situated in close proximity to each other, it is advisable to sort out certain maximums. Thus, when searching for maximums, it is permissible, if a maximum $M_s$ in the strict sense is found, also to go over to neighbors (or their neighbors etc.) with lower z coordinates, as long as the difference of the z-coordinates of this point and $M_s$ does not exceed a certain quantity, such as 0.25 mm in the case of teeth. If a path to a point with a z coordinate greater than $M_s$ is found in this manner, $M_s$ should be sorted out and removed from the list of maxima.

Only the remaining maximums, and their expanded catchment areas, are considered in the following procedures 310, 312 and 314 of FIG. 11.

The number of maximums can vary between about 30 (between 1 and 4 maximums on each tooth crown) and 100 (scan with brackets, many gaps, very non-smooth surface). T0, T1, T2 may be contained in the list of maximums, but the processing do not care about that. Every point in the virtual model belongs to exactly one catchment area.

The flow chart of FIG. 13 shows the process 308 as including step 340, determining whether there is a point in the surface which has not been passed yet in the traversal of the triangle edges. If so, at step 342 a check is made to see if the point has a neighbor with a greater Z value. If so the process proceeds to step 344 and the search continues to the next adjacent point with a greatest Z value, and processes 342 and 344 continued until a local maximum is reached. Once the local maximum is reached, block 342 is answered in the negative, and so the point is marked as a local maximum at step 346 and the process proceeds to step 348 were all the points that were passed in steps 342 and 344 are marked as belonging to the "catchment area", the area bounded by the local maximum. The process reverts back to step 340, another available point is selected, and the process continues until all points have been tested, at which the process finishes, as indicated at step 350. The resulting maxima 500 are shown in FIG. 18. The catchment areas for the local maxima are given different shading, including areas 502, 504, 506, 508, 510, etc. Each local maximum has one and only one catchment area.

The sorting of the local maxima, described above, does not appear in the flow chart since the flow chart would have been unnecessarily long and more complex otherwise. On the other hand these sorting out mechanisms are very heuristic and not a substantial part of the whole process. The whole process can easily be performed without this sorting out, it will only take longer.

Figure 19:
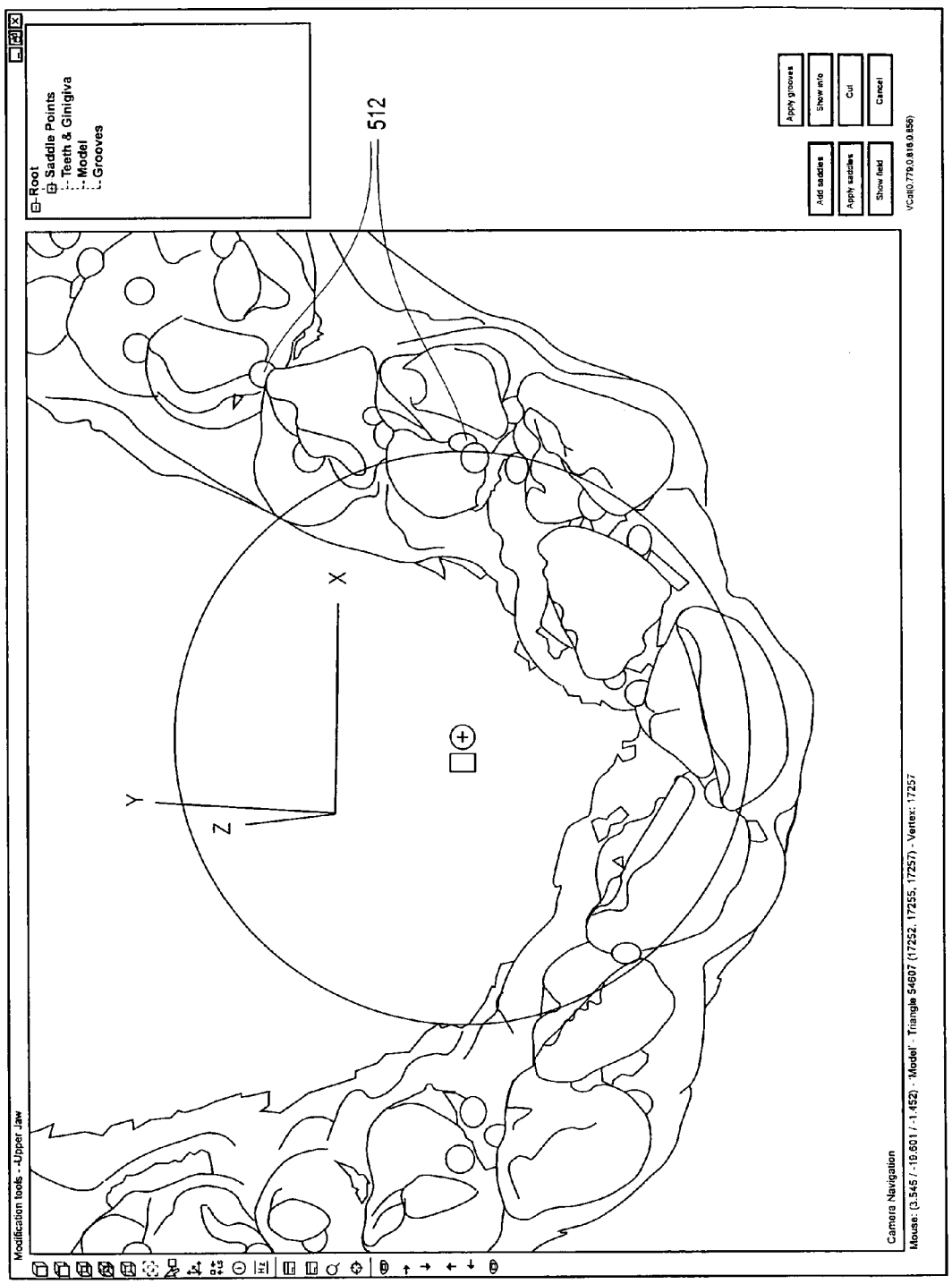
FIG. 19 is a screen shot showing the positions of the saddle points, identified as a result of the operation of process 312 of FIG. 11.

Finding Saddle Points (310) (FIG. 19)

Referring again to FIG. 11, the process continues with a step 310 of finding saddle points. Saddle points are shown as item 512 in FIG. 19. They correspond to boundaries between teeth, and to some extent boundaries between local maxima. They are defined as follows: Given two maximums $M_i$ and $M_j$. Construct a string of points $W_{ij}$ from $M_i$ to $M_j$, i.e., a string of points connecting the two maximums via neighborhoods. Such a path has one point $V_{low}$ with the smallest z coordinate of all points of the path. There is (at least) one path from $M_i$ to $M_j$ whose $V_{low}$ that has the largest possible z coordinate (i.e., there is no other path from $M_i$ to $M_j$ whose $V_{low}$ has a larger z coordinate). We call this $V_{low}$ "saddle point" $S_{ij}$.

All possible saddle points $S_{ij}$ differing in pairs from other saddle points now make up the quantity of saddle points $S=\{S_0, \ldots, S_s\}$. 'Differing in pairs' just means 'not equal to each other': If, e.g., $S_{3,6}$ is equal to $S_{5,9}$ (which may happen, because $W_{ij}$ are not necessarily disjoint), we do not list both, but only one of them. According to the above definition there could be more than one saddle point corresponding to $M_i$ and $M_j$. In practice we chose any one of them.

Normally, there is at least one maximum on the crown of each tooth; molars and premolars usually have several. The saddle points between the maximums of adjoining teeth mark, relatively precisely, the places "between" the teeth. These points are later used as starting points for detecting ravines, a process described in conjunction with FIGS. 14–16.

The method for finding saddle point candidates is as follows. All triangle edges whose one vertex belongs to the catchment area of the maximum $M_i$, the other vertex to the catchment area of $M_j$, form the boundary between the two catchment areas. The lower vertex (the vertex with the smaller z coordinates) of the highest edge of this boundary is a saddle point candidate $K_{ij}$.

The process proceeds with a sorting out process for saddle point candidates. Not every one of these saddle point candidates is a saddle point. Because if there is a path from $M_i$ to $M_j$ via other catchment areas without having to pass a saddle point (candidate) which has a smaller z coordinate than $K_{ij}$, then $K_{ij}$ is not a saddle point. This is determined by means of a tree search from each catchment area i to every other catchment area j.

Figure 20:
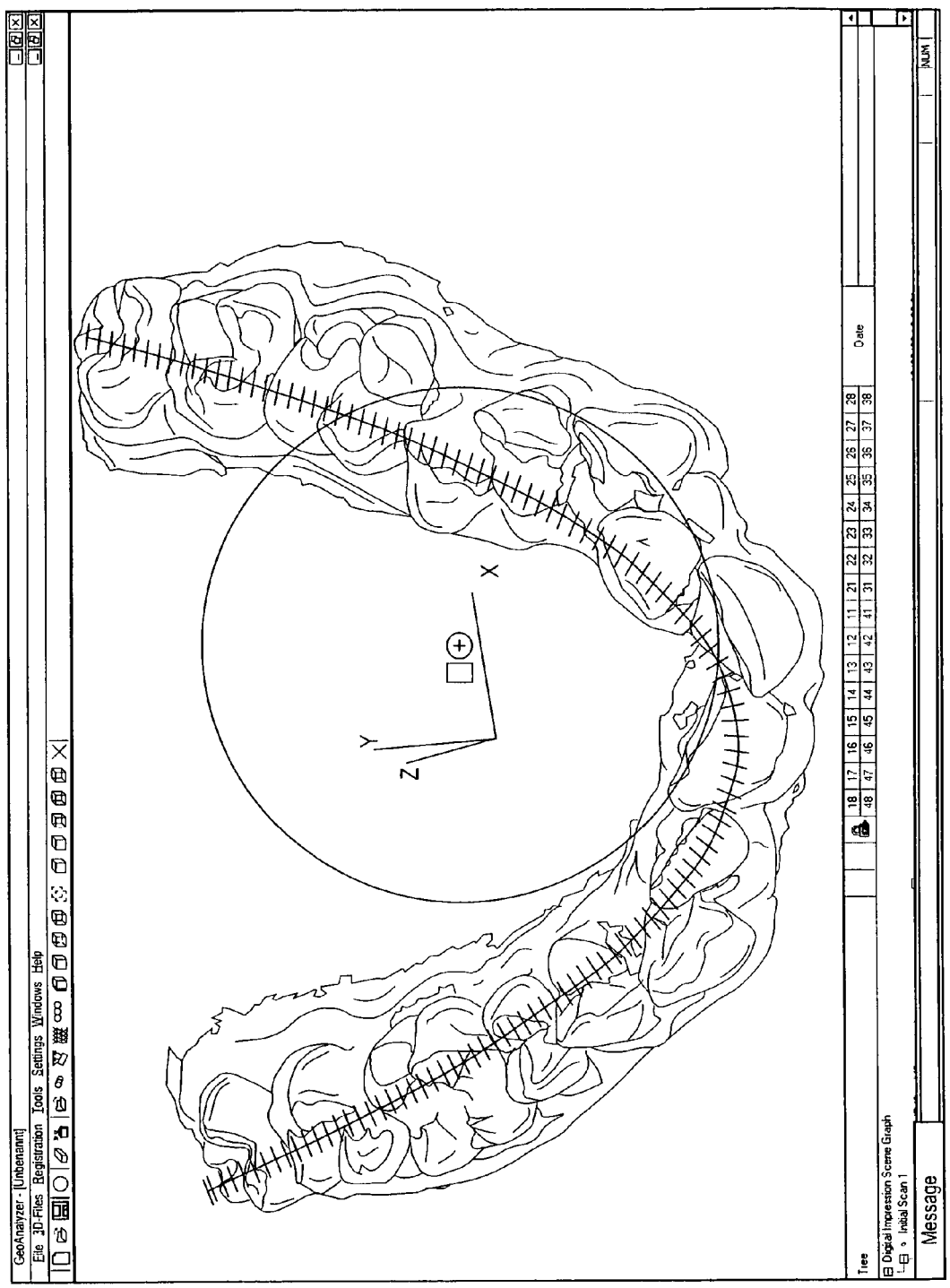
FIG. 20 is a screen shot showing the virtual model with an arch form placed thereon, illustration showing both the axis and scale of the arch form.

Determine Location of Saddle Points on Arch Form (e.g., Parabola) (312)(FIG. 20.)

The process of FIG. 11 proceeds to a step of determining the location of the saddle points on an arch form. The illustrated method uses a parabolic coordinate transformation in which the arch form is represented as a parabola 514.

The aim of procedure 312 is to arranging saddle points along a dental arch. A parabolic system of coordinates is helpful in arranging the saddle points along the dental arch and, later on, in measuring the "width" of an area (=extension along the dental arch). For this purpose, a parabola is placed on the x-y plane in such a manner that its axis lies on the y axis, the apex has the y coordinate of the maximum $M_i$, with the smallest y coordinate, and that the distance from the parabola to all the other maxima $M_i$ is as short as possible. This parabola roughly follows the dental arch, its apex being situated at the front teeth. This is shown in FIG. 20. When we refer to the shape of the parabola being one in which distance from the parabola to all further maximums is as short as possible, it is not necessary to find one with this exact property. A rough approximation is sufficient.

A suitable formula for defining the shape of the parabola is as follows:

par: $y=ax^2+b$, where b is defined by the apex (as explained above), and $$a = \frac{\sum_{j \in J} \frac{M_y^j - b}{(M_x^j)^2}}{|J|},$$

where $M_j=(M_x^j, M_y^j)$ are the Maximums, and $$J = \{j | M_y^j > b + 8.0\}$$

In the parabolic coordinate transformation, a parabolic x coordinate is now calculated to each vertex V of each triangle in the virtual model. The parabolic x-coordinate is the (signed) arc length of the parabola from the apex to the base point of V (i.e., the point of the parabola closest to V). The parabolic x-coordinates of the saddle points are used in the subsequent procedures for forming a path that links the saddle points and separates the tooth crowns from the gingival tissue, as will be apparent from the discussion below. With the transformation performed (including the transformation of the saddle points), the parabolic x-coordinates for the saddle points make it possible to sort the saddle points into a saddle sequence and measure approximate lengths along the dental arch.

It will be appreciated that the parabolic transformation in step 312 could be performed for all points in the model first, and then the saddle points determined, or the other way around. Either way, once the saddle points have been determined and the parabolic transformation performed, the x-coordinates of the saddle points will be known and thus the sorting of the saddle points along the arch form can be performed.

Perform Automatic Area Search (314) (FIG. 14)

Referring back to FIG. 11, after the location is found of the saddle points on the parabola using the parabolic x-coordinates, the process 300 proceeds to a final step 314 of performing an automatic area search. This step 314 is shown in flow chart form in FIG. 14.

The aim of the automatic area search process 314 is to find a sequence of saddle points in which two successive saddle points are on opposite sides of each tooth. The areas between the successive saddle points then correspond to a tooth crown. This sequence of saddle points is generally a partial sequence of the saddle sequence (i.e., the sequence of all saddle points arranged according to parabolic x coordinates).

The main idea of the process 314 is to perform a tree search over all possible partial sequences of the saddle sequence, calculate of a quality for each such partial sequence (measure of plausibility), and select of best partial sequence. The quality of each partial sequence is determined as follows. The area width deviations from an average width typical of the type of tooth concerned, and the height of the area, are among the factors taken into account for each area between two successive saddle points. The sum of the deviations is the quality of the partial sequence.

In performing the tree search, a breakoff criteria is used. The tree search has to be broken off prematurely at different points in order to arrive at a result within a reasonable length of time. This is done, if e.g., an area cannot be marked off between two successive saddle points, there is (excessive) overlapping of two successive areas (areas between three successive saddle points) (this is the case, e.g., when all three saddles lie in the region of one tooth), or if the distance between two successive saddle points becomes too large (in excess of a multiple of the maximum expected tooth width).

Since many areas $G_{ij}$ occur in different branches of the search tree, it is advisable to save areas that have already been calculated. This is done with the aid of a map. This map assigns no or exactly one elementary area to each triangle of the scan. A quantity of elementary areas is now assigned in turn to each calculated area. All areas that have already been calculated are indexed in a matrix (number of saddle points X number of saddle points). In this way, the area $G_{ij}$ can be retrieved for each $S_i$, $S_j$ pair if it has already been determined. The map is also a convenient means of determining overlaps of two areas (quantity of elementary areas contained in both areas).

With reference now to the flow chart of FIG. 14, the process starts at block 430 and proceeds to step 432. An initial saddle point S is selected. The process proceeds to step 434, where a test is conducted to see if there is another saddle T which lies on one side of S, as defined by a search direction. If so the process proceeds to step 432 where the breakoff criteria is tested. If the saddle point T is within the breakoff criteria, a delimitation of the area between S and T is made in module 438. This module 438 is described in FIG. 15 and will be explained subsequently. The process proceeds to step 440 to determine whether the delimitation of the area in step 438 was successful. If so, the processing proceeds to step 442, where a check is made to see if there is excessive overlapping of the new region and the neighboring region. If no excessive overlapping is found, the quality of the current sequence of regions is calculated at step 443 and the result is stored. The starting saddle point S is added to a stack comprising a partial sequence of the full saddle point sequence. In module 443, the "current sequence of regions" corresponds to the current. sequence of saddles, i.e., all saddles in the stack, from the bottom of the stack to the top, including the saddles S and T.

If either block 434 or 436 results in a negative response, the processing proceeds to block 444, where the process checks to see if the stack is empty. If no, the process proceeds to block 446 and saddle S is removed from the stack and the process goes back to block 434. If, at block 444 the stack is empty, the process proceeds to bock 448 and a test is made to see if there is another available starting saddle. If so, the process proceeds to loop back to block 432, If not, the process ends by choosing the sequence of regions with the best overall quality (stored in block 442). In this sequence of regions (areas), each region (area) corresponds to a tooth crown.

A. Delimitation of an Area Between Two Saddle Points (438)(FIG. 15)

Figure 15:
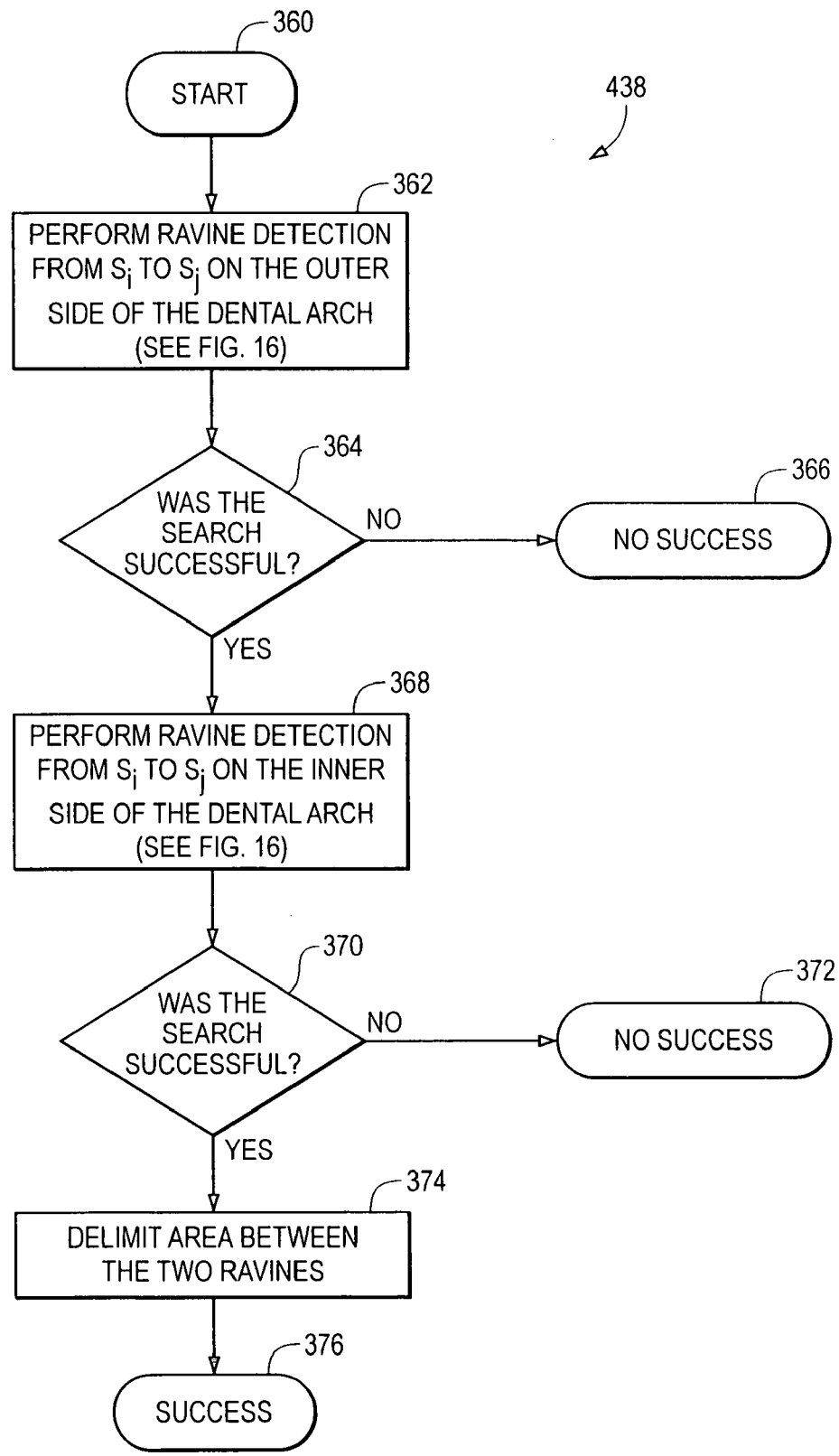
FIG. 15 is a flow chart of the process 434 of FIG. 14, which is executed in software for delimiting an area between ravines that are identified which connect saddle points; the delimited areas define a tooth crown or portion thereof. The process

The module 438 of FIG. 14 is shown in more detail in FIG. 15. The idea of module 438 is that given any two saddle points $S_i$ and $S_j$, two ravine detection operations are carried out from $S_i$ to $S_j$, one on the outer side of the dental arch, the other on the inner side of the dental arch. If both detection operations prove successful, there are two series of triangle edges or lines linking $S_i$ and $S_j$. If the two series of lines intersect (or if they do not intersect only within a short distance from $S_i$ and $S_j$, such as 10 triangle edges), an area $G_{ij}$ can be marked out between them. The area $G_{ij}$ comprises area formed by triangles of the scan that are situated between these edges or the vertices referenced by these triangles. The properties such an area has include:

Width: Difference between the largest and the smallest of all parabolic x coordinates of all vertices contained in the area.

Height: Largest z coordinate of all vertices of the area (local maximum).

Figure 16:
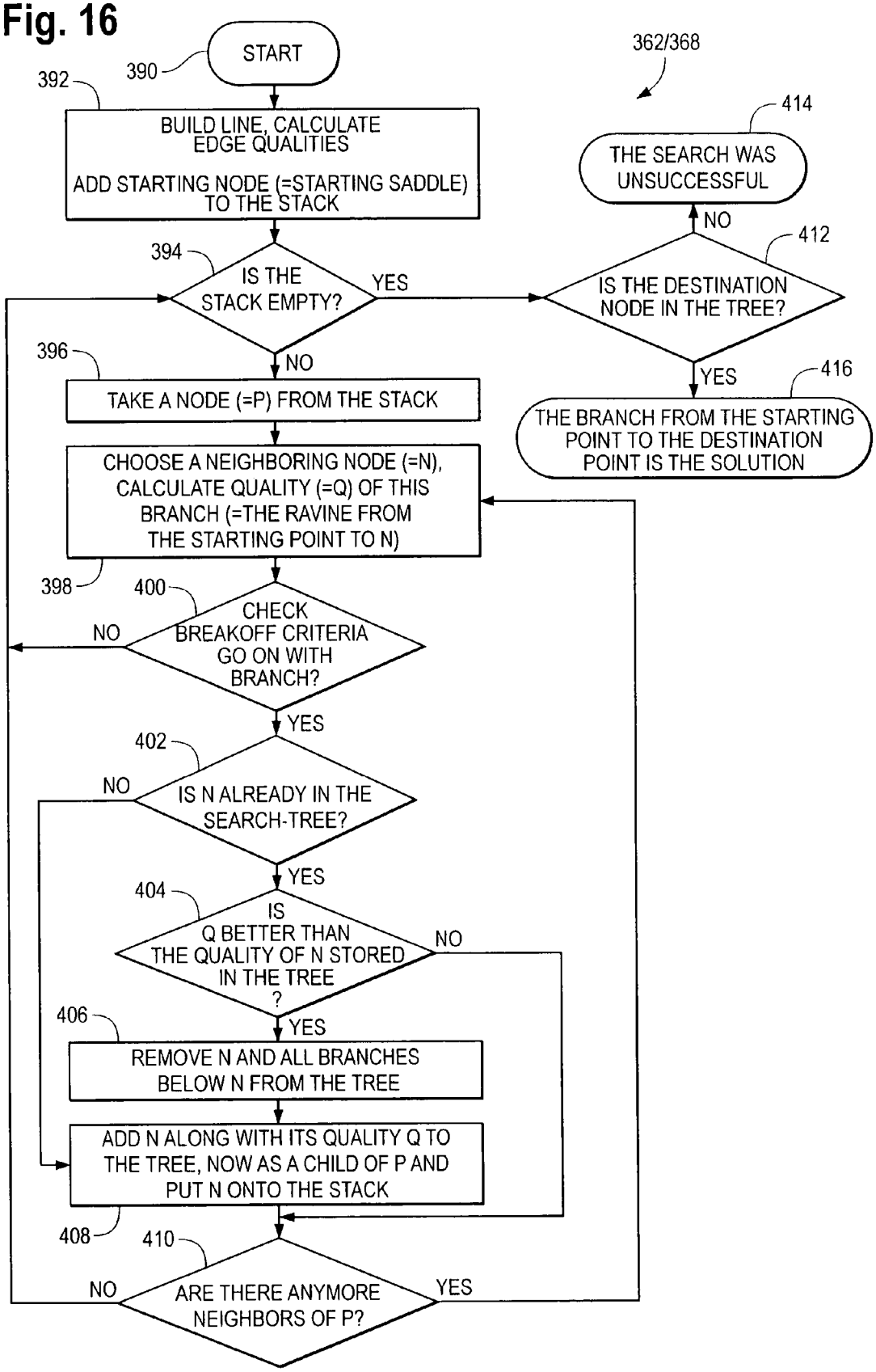
FIG. 16 is a flow chart of a process executed in software for ravine detection, the process of FIG. 16 being a subroutine of the area delimiting process of FIG. 15.

The process of delimitation of an area 438 will now be explained with reference to the flow chart of FIG. 15. The start 360 is from the module 436 of FIG. 14. At step 362, a ravine detection algorithm is made from saddle point $S_i$ to saddle point $S_j$ on the outer side of the tooth. The ravine detection algorithm follows uses a curvature feature to follow concave curvatures (ravines) between the saddle points, taking advantage of the observation that the areas between teeth and gums is bounded by concave curvature. The ravine detection process is shown in FIG. 16 and will be described subsequently. A check is made at block 364 to see if the ravine detection process was successful. If it was not successful, as indicated at 366, the processing at block 440 of FIG. 314 reverts back to the NO branch and the module 434 executes again.

If the ravine detection algorithm 362 of FIG. 15 is successful, the process proceeds to block 368. Another ravine detection process 368 is performed from saddle point $S_i$ to saddle point $S_j$ on the inner side of the dental arch. Again, the ravine detection subroutine 362/368 of FIG. 16 executes. At step 370 a check is made to see if the search was successful. It was not successful, the processing proceeds as indicated at a 372 and block 440 of FIG. 14 is answered in the negative.

If the search at 368 was successful, the area Gi,j between the two ravines is delimited and the success of the procedure is noted at step 376. This success at step 376 is used by block 440 in FIG. 14 to determine whether to proceed with the following module 442.

B. Ravine Detection (362/368)(FIG. 16, 22-25)

The aim of the ravine detection process 362/368 of FIGS. 15 and 16 is the determination of the transitions between teeth and gum and between adjoining teeth. As a rule, there is a ravine between a tooth and the gum tissue. If adjoining teeth touch, their transitions also form ravines on the scan surface. However, there can be marked differences between these ravines, or they can be altogether absent in some places. Ravines can also form on the gum or tooth surface. For this reason it is important to carry out a directional ravine detection procedure, the specific objective being to detect ravines forming a roughly arch-like link between two saddle points (the starting point and target or end point of the algorithm). If the two saddle points mark a tooth's boundary with its neighbors and if two such ravines are found—one on the outer, the other on the inner side of the dental arch—, then that portion of the scan that matches this tooth is bounded by these ravines.

The basis of the underlying ravine detection process is a line or path that is constructed along the vertices or nodes of the triangles in the mesh surface. An edge between two nodes corresponds either to a triangle edge or to the imaginary line linking two vertices, which are edge points of one and the same hole. (This second kind of edge makes it possible for the ravine search to be done even through holes.) The algorithm further uses local curvature to find the line that follows the "bottom" of the ravine. In particular, based on the angle of the triangles adjacent to the edge that is used for the line, and the size of such triangles, a local surface curvature is calculated for each edge of the line that corresponds to a triangle edge.

The local curvature to find the path following the "bottom" of the ravine is defined as follows. If we have 2 triangles i, j, and their normalized normal vectors $\vec{n}_i$, $\vec{n}_j$, and the points $P_n$ and $P_m$ which form the common edge of the triangles i and j, then the curvature c is defined:

$$c = \vec{n}_i \cdot \frac{(P_m - P_n) \times \vec{n}_j}{\|(P_m - P_n) \times \vec{n}_j\|}$$

A vector field (FIG. 22) is used which assigns a direction to each point of the surface. The vector field is used in the quality criteria to direct the ravine search such that the successful path describes an arc from the starting saddle point to the target saddle point. The vector field is based on a circle which is constructed through the starting point and the target point and which is tilted to the outside or to the inside. Whether it is tilted to the outside or the inside and the field's sense of rotation depend on whether the search is to be carried out on the outer or the inner side of the dental arch. The circle is tilted by 45°, once clockwise, once counter-clockwise (for the 'inside' ravine, which means the lingual transition between crown and gingiva, and the 'outside' ravine, which means the labial transition between crown and gingiva).

In the ravine detection method, a tree search is now carried out along a path traversing edges of triangles, starting from the starting point, saddle point $S_i$. A quality can be assigned to each edge (triangle surface edge) of the line. Two qualities are determined: the curvature of the edge (concavity) and the angle formed between the edge and the vector field at the starting point of the edge (parallelism). The quality of a branch of the search tree is obtained by adding the qualities of all edges from the root (starting point) to the end of the edge—multiplied by their lengths—and dividing them by the total length of the branch.

We now search for that branch from among all the branches which reach the destination point, which has the highest quality at the destination point. If a complete search cannot be carried out within a reasonable length of time, the search is broken off prematurely at numerous places. Thus, this process does not, in general, find the very best solution, but one of the best solutions, which is enough for the present purposes to result in a correct gingival tissue/tooth separation. Some of the breakoff criteria which are used are: (1) a branch is not continued if another branch leading to the same branch ends but one with a better quality has been found, and (2) a branch is not continued if a maximum length is exceeded, a minimum quality is fallen short of, or a certain start or target-point environment is departed from.

Figure 21:
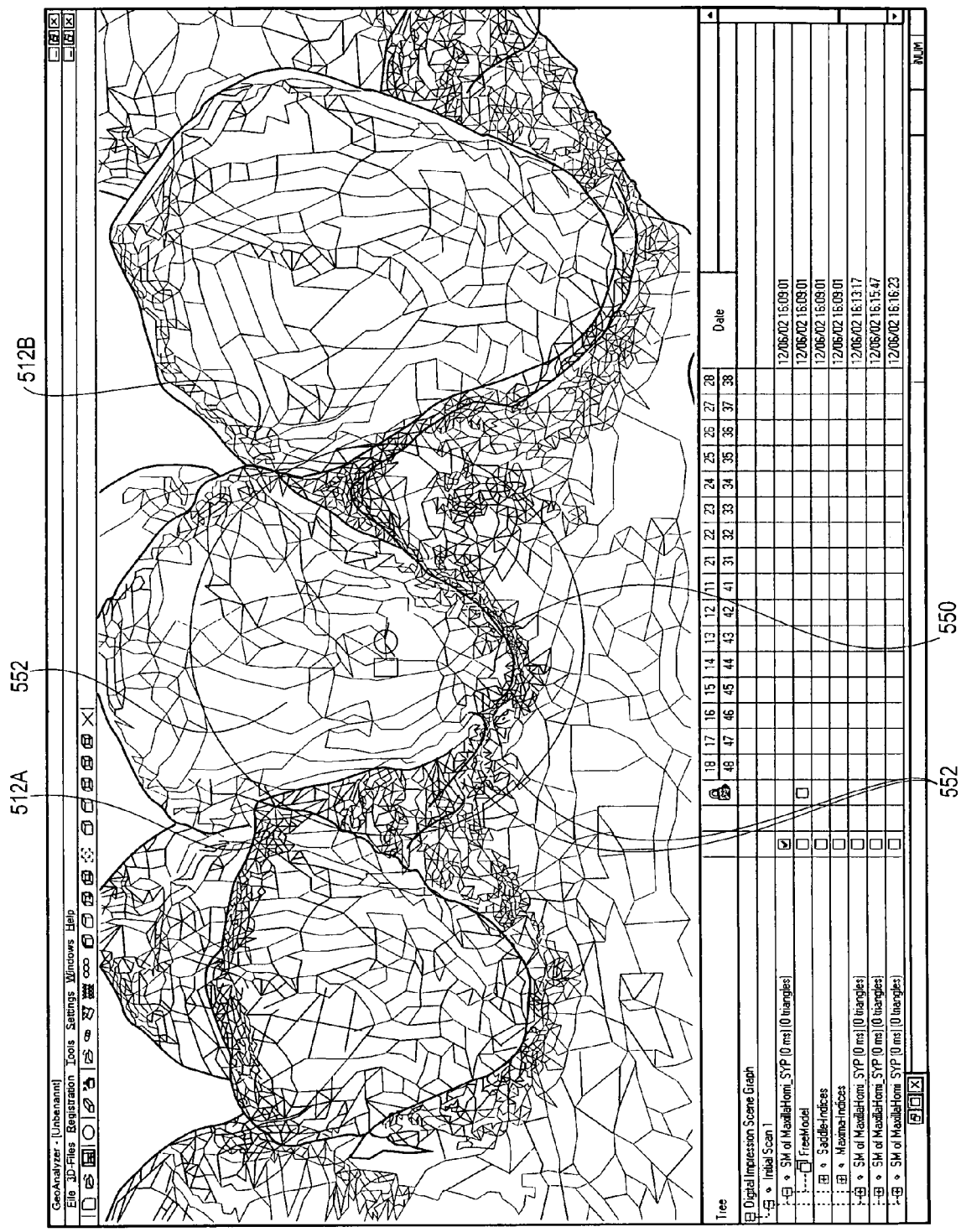
FIG. 21 is a illustration of a portion of the model showing the "ravine" areas which comprise the boundary between the gingival and the tooth crowns. The area in the vicinity of the ravine has a curvature that is either convex or concave; the concave curvature is used a means for finding a path between saddle points positioned around the tooth crown.
Figure 22:
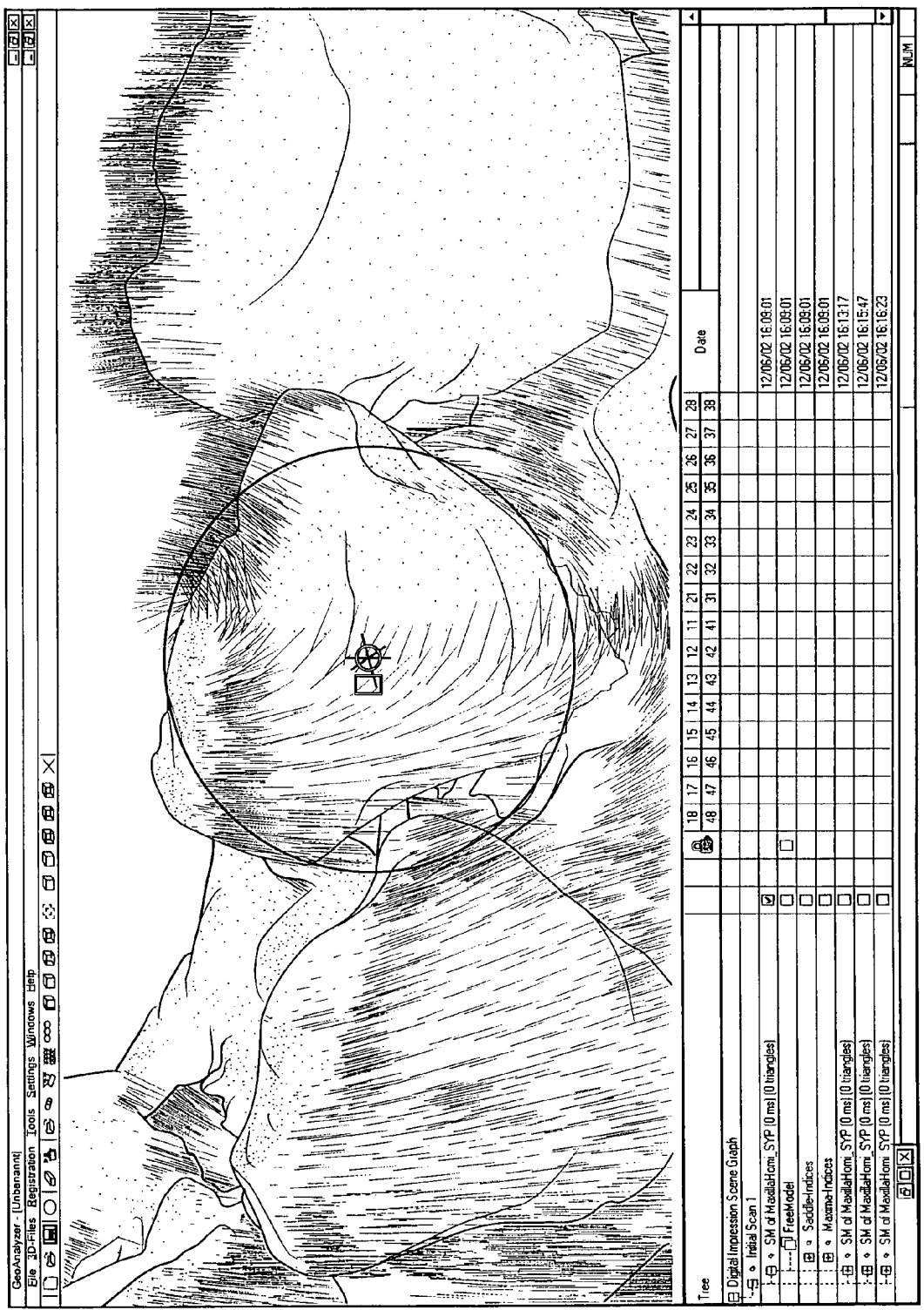
FIG. 22 is an illustration of a vector field that is used to guide the direction of the ravine detection process.
Figure 23:
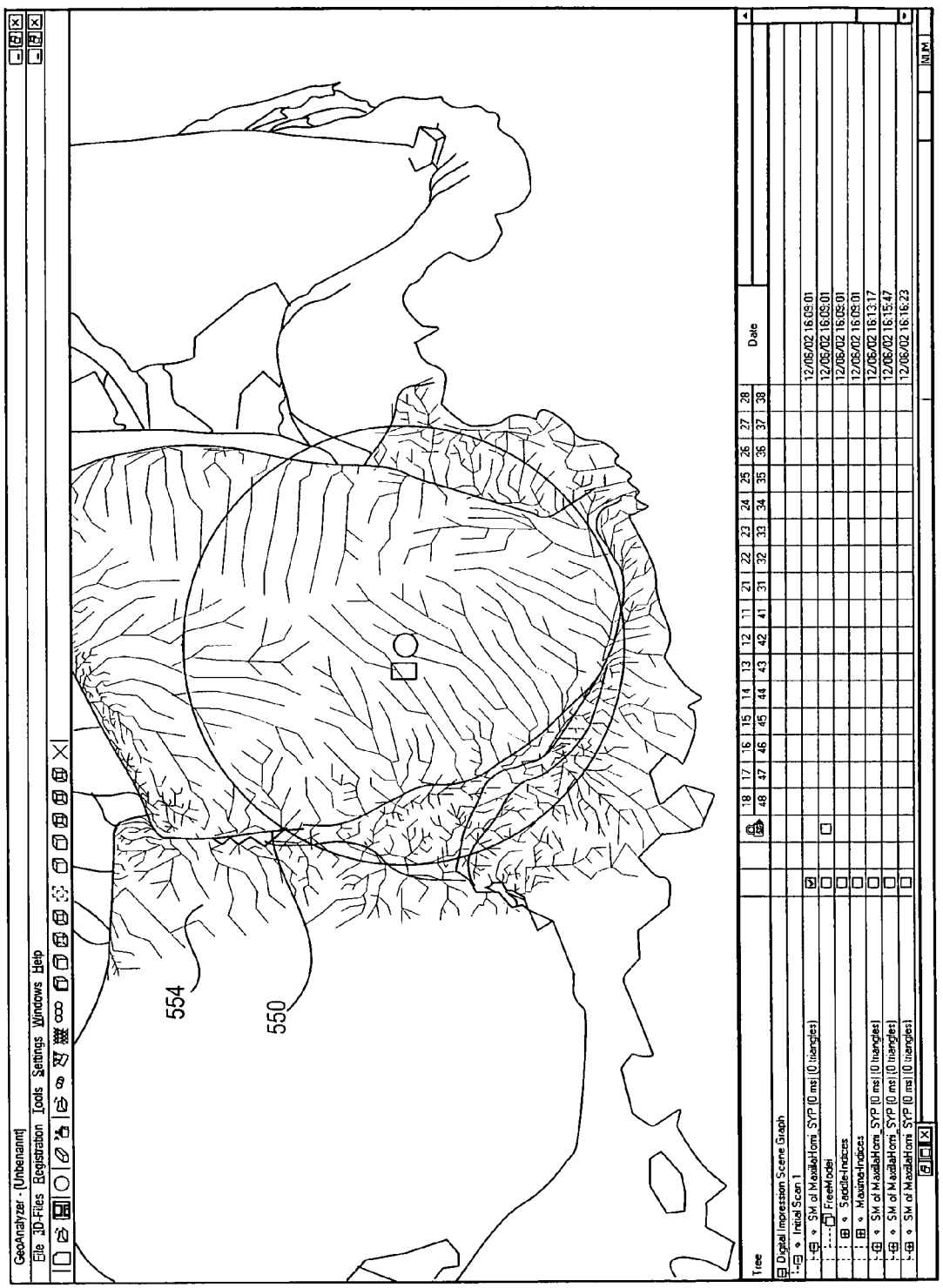
FIG. 23 is an illustration showing search trees that attempted to find a path (i.e., a line or curve along edges of triangle surfaces forming the surface of the model) along a ravine to link saddle points, in accordance with the processes 362 and 358 of FIG. 14 and FIG. 15.
Figure 24:
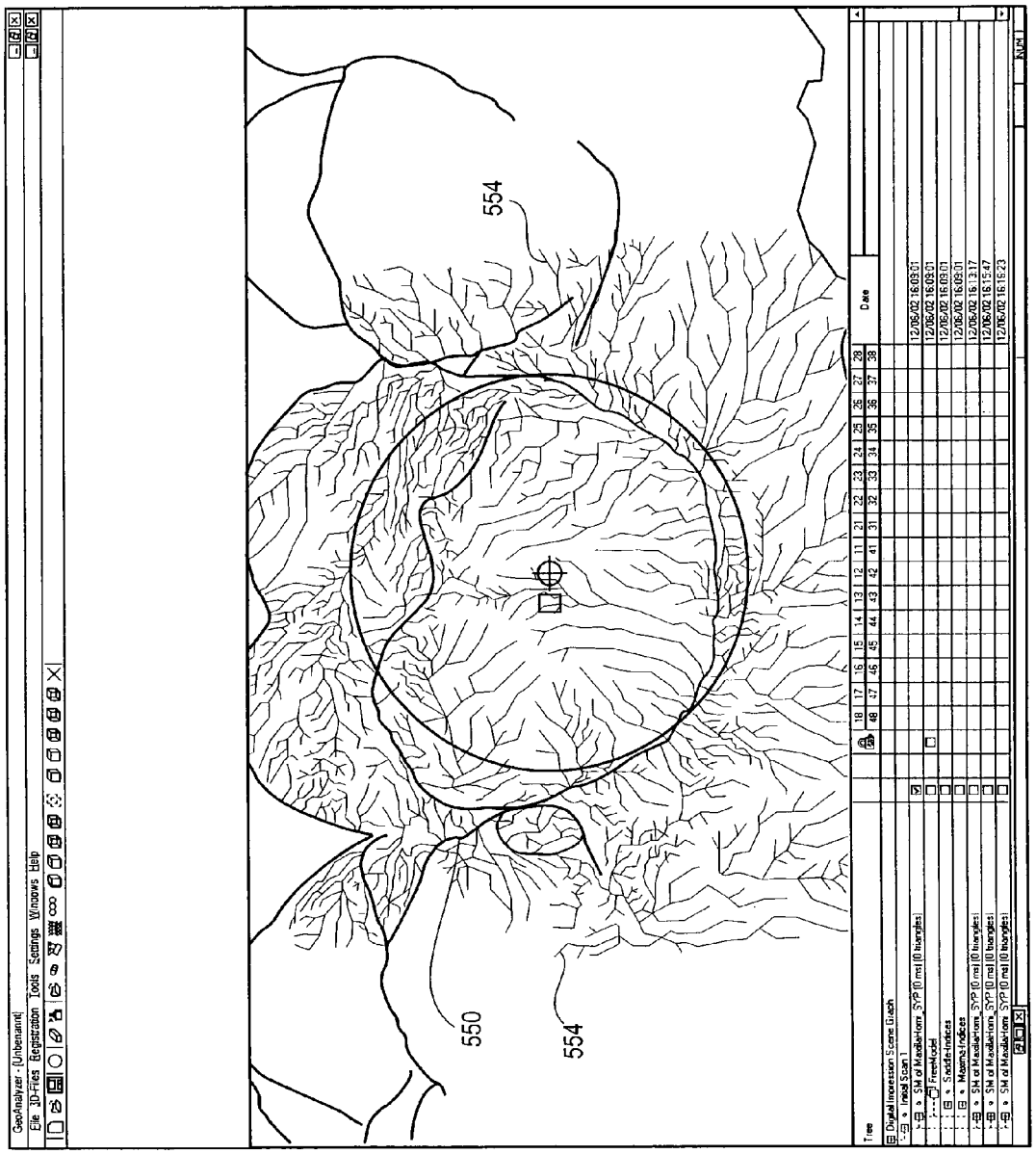
FIG. 24 is another illustration showing search trees which are attempted to find a path along a ravine to link saddle points.
Figure 25:
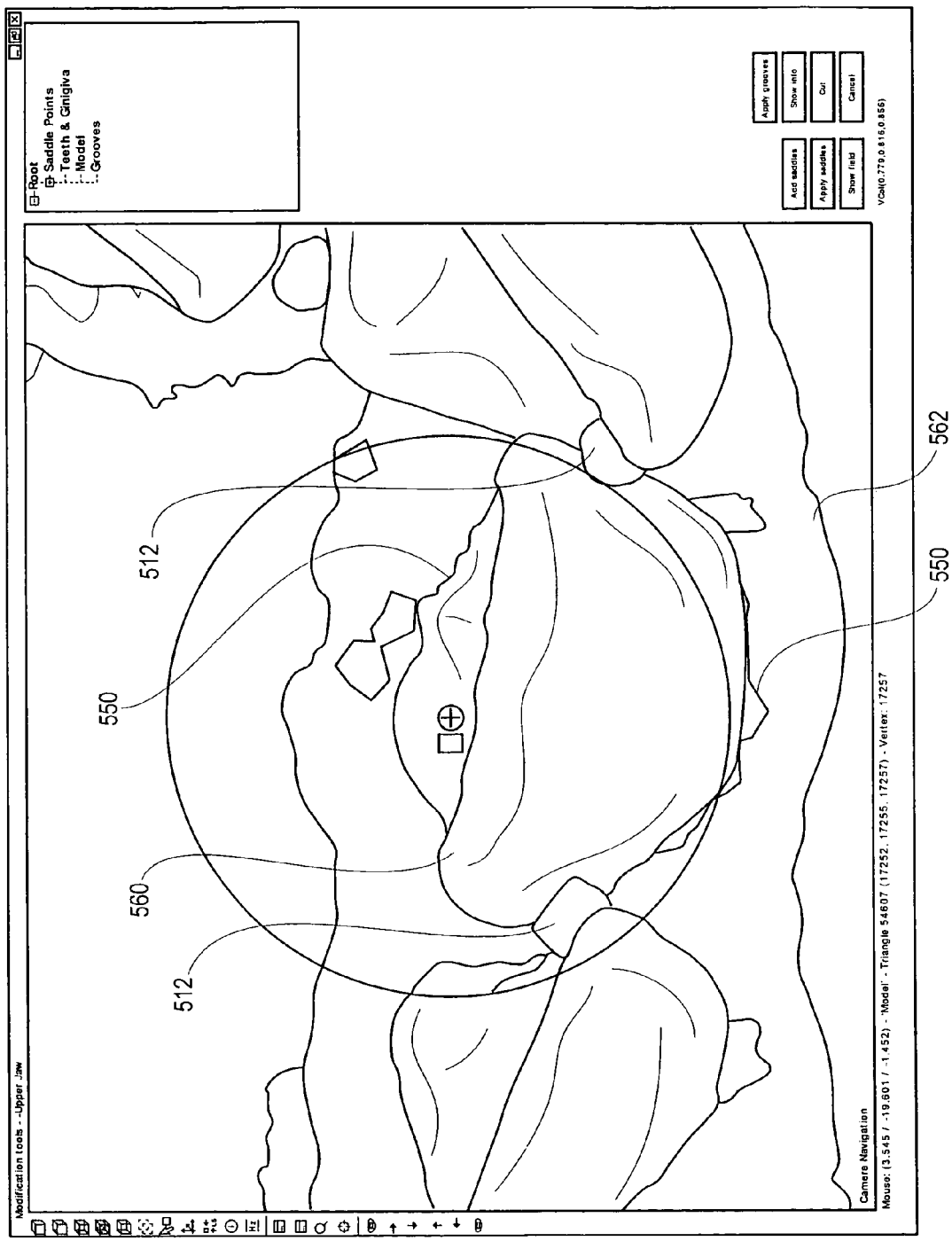
FIG. 25 shows the results of the delimitation of an area process of FIG. 14, showing the crown of the tooth, the saddle points, and the boundaries of a ravine that encircles the crown of the tooth.
Figure 26:
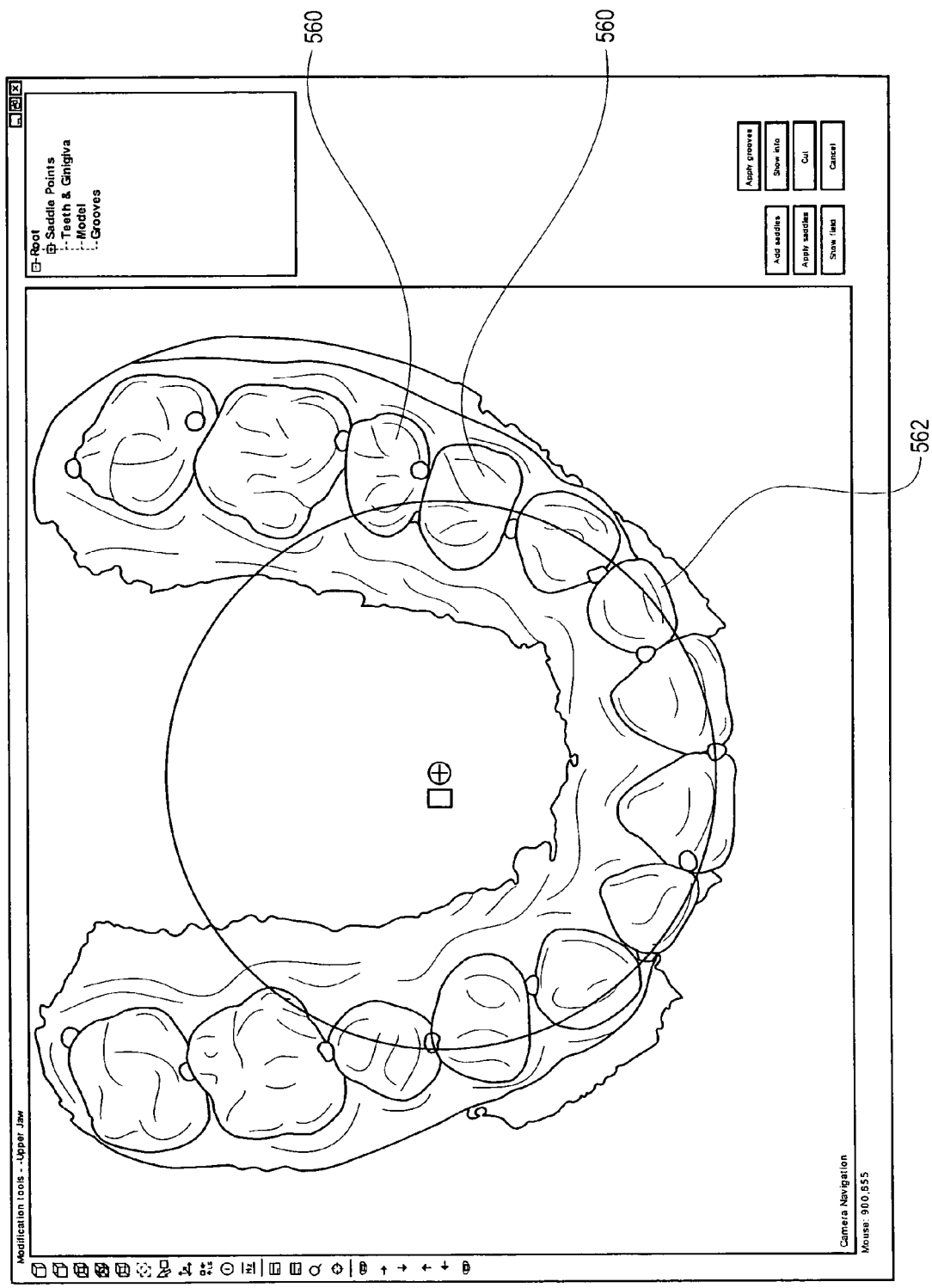
FIG. 26 shows the results of the crown detection process of FIG. 11: a model of the dentition with a plurality of individual tooth crowns isolated (bounded) and identified as individual objects, and the remaining structure identified as gingival tissue.

FIG. 21 shows two saddle points 512A and 512B on opposite sides of a tooth. The lines 552 are color-coded light blue on the display to show local convex curvature, whereas the faint lines in the region of the line 550 are in a contrasting color (e.g., red) to show a concave curvature. One line 550 has been found in the ravine detection process which meets are the search and quality criteria, and which successfully links saddle points 512 A and 512 B. The vector field of FIG. 22 provides directional criteria for the search for the line 550. In FIG. 23, the lines 554 show all the branches in the tree search that are searched. All but one branch in the tree eventually terminates when the quality criteria are not satisfied. The line 550 meets all the criteria and links the saddle points on opposite sides of the tooth. Another illustration of the tree search and the line 550 meeting the search and quality criteria is shown in FIG. 24. FIG. 25 shows the two lines 550 extending between the saddle points 512 on opposite sides of the tooth, showing the area 560 bounded by the lines and extending in the positive Z direction corresponding to the tooth crown, and area 562 extending in the negative Z direction corresponding to gingival tissue. FIG. 26 shows the process applied to the entire dental arch, showing crowns 560 that are identified by the process described herein and the gingival tissue 562.

Referring now to the flow chart of FIG. 16, the ravine detection process starts at 390, and is entered from the procedure 438 of FIG. 15 at either module 362 or 368. The process proceeds to block 392, where beginning of the line (branch) is constructed, and the edge qualities (curvature) is calculated. The starting point (saddle point) is added to a "stack" comprising a list of points in the tree search.

The process proceeds to step 394, and a check is,made to see if the stack is empty. If not, the process proceeds to step 396, where a node (starting point) is selected from the stack. At step 398, a neighboring point N in the mesh is chosen and a calculation is made of the quality Q of the branch (the ravine or series of interconnecting triangle edges from the starting point to the point P). At step 400, a check of the breakoff criteria is performed. If the check is satisfied, the processing proceeds to block 402, which checks to see if the point P is already in the search tree. If so, the processing proceeds to block 404, where a test is made of the quality Q to see if it is better than the quality for the neighboring point N that is already stored. If the quality is better, the process proceeds as indicated at step 406 by deleting the point N and all branches below N from the tree that were previously stored, and proceeding to module 408 where N is added along with quality Q to the tree, where the point N is added as a child or branch from point P and point N is added to the stack.

If, at point 402 the neighboring point P was not already in the search tree, the process proceeds to step 408 as indicated in FIG. 16.

If, at step 406, the quality Q of point N is not as good as the quality of N already stored in the processing proceeds to block 410. The processing from module 408 also proceeds to block 410, as shown in FIG. 16. At block 410, the processing sees if there are any more neighbors of P. If so, the processing loops back to module 398 and the following steps are conducted again. If there is no neighbor of P, the process goes back to step 394.

Eventually, the process of FIG. 15 will attempt to construct a line connecting all possible paths between the starting saddle point and the target point, another saddle point. This is indicated by the processing looping back to step 394, where a check is made to see if the stack is empty. If so, the processing proceeds to step 412, where a check is made to see if the destination node (other saddle point) is in the tree. If so the branch (or line) from the staring point to the destination point is the solution, and this line or branch is saved at module 416. If the destination point is not in the search was unsuccessful, as indicated at block 414, and a negative result is returned to module 438 (FIG. 15) at block 364.

From the foregoing discussion, it will be appreciated that in yet another aspect of the invention, we have described a ravine detection invention that provides instructions for execution by a programmed computer that identifies a path interconnecting saddle points between virtual teeth in a virtual model of the dentition. The path comprises a transition between teeth and gingival tissue and between adjacent teeth in a virtual model of dentition. In a preferred embodiment, as explained in FIG. 16, the path is determined by performing a tree search, and wherein the tree search is performed by reference to local curvature of the virtual model and a vector field for the model defining a direction of search for the path.

Persons skilled in the art will appreciate that variation from the details of the presently preferred embodiment may be made without departure from the true scope of the invention. This true scope is to be determined by reference to the appended claims.

The invention claimed is:

1. A method for automatically identifying tooth crowns in a virtual three-dimensional model of teeth in a dental arch, comprising the steps of:
   a) storing said model in a memory accessible to a general-purpose computer, said computer including a processing unit;
   b) providing machine readable instructions for execution by said processing unit, said instructions comprising instructions operating on said model in the following respects:
      1) orientating said model with reference to a plane;
      2) automatically determining local maxima of the model and areas bounded by said local maxima;
      3) automatically determining saddle points between said local maxima in the model, said saddle points corresponding to boundaries between teeth;
      4) determining the position of said saddle points along a dental archform, and
      5) for each tooth, automatically identifying a path linking said saddle points comprising a transition between teeth and gingival tissue and between adjacent teeth in said model, and identifying areas bounded by said path and in the direction of said plane as corresponding to one of said tooth crowns.

2. The method of claim 1, wherein instructions 1) comprises instructions defining an occlusal plane or approximation thereof for the model and an approximate center of the model, and performing a transformation of said model to thereby orient said model with reference to said occlusal plane or approximation thereof and to said center.

3. The method of claim 1, wherein, in instructions 4), said archform comprises a parabolic archform of the form $y=ax^2+b$, and wherein the method further comprises the step of performing a parabolic coordinate transform to thereby determine parabolic x coordinates for said saddle points.

4. The method of claim 1, wherein said instructions 5) comprises instructions:
   1) performing a directional ravine detection process testing for paths between saddle points with a concave curvature between two saddle points; and
   2) delimiting an area bounded by said paths if said ravine detection process is successful.

5. The method of claim 1, wherein instructions 2), 3), 4) and 5) operate on a representation of said model comprising a continuous single surface formed of interconnected triangles defined by vertices.

6. A method for automatically identifying gingival tissue in a virtual three-dimensional model of anatomical structures of the teeth and associated gingival tissue in a dental arch, comprising the steps of:
   a) storing said model in a memory accessible to a general-purpose computer, said computer including a processing unit;
   b) providing machine readable instructions for execution by said processing unit, said instructions comprising instructions operating on said model in the following respects:
      1) orientating said model with reference to a plane;
      2) automatically determining local maxima of the model and areas bounded by said local maxima;

3) automatically determining saddle points between said local maxima in the model, said saddle points corresponding to boundaries between teeth;
4) determining the position of said saddle points along a dental archform, and
5) for each tooth, automatically identifying a path defining comprising a transition between teeth and gingival tissue and between adjacent teeth in said model and linking said saddle points, and identifying areas bounded by said path and in the direction away from said plane as corresponding to said gingival tissue.

7. The method of claim 6, wherein instructions 1) comprises instructions defining an occlusal plane or approximation thereof for the model and an approximate center of the model, and performing a transformation of said model to thereby orient said model with reference to said occlusal plane or approximation thereof and to said center.

8. The method of claim 6, wherein, in instructions 4), said archform comprises a parabolic archform of the form $y=ax^2+b$, and wherein the method further comprises the step of performing a parabolic coordinate transform to thereby determine parabolic x coordinates for said saddle points.

9. The method of claim 6, wherein instructions 5) comprises instructions:
   1) performing a directional ravine detection process testing for paths between saddle points with a concave curvature between two saddle points; and
   2) delimiting an area bounded by said paths if said ravine detection process is successful.

10. The method of claim 6, wherein instructions 2), 3), 4) and 5) operate on a representation of said model comprising a continuous single surface formed of interconnected triangles defined by vertices.

11. In a system comprising a programmed computer containing instructions for separating virtual teeth from a virtual model of both teeth and gingival tissue, the improvement comprising:
   providing instructions for execution by said programmed computer that 1) automatically determine local maxima of the model and areas bounded by said local maxima;
   2) automatically determine saddle points between said local maxima in the model, said saddle points corresponding to boundaries between teeth;
   3) automatically determine the position of said saddle points along a dental archform, and
   4) for each tooth, automatically identifying a path interconnecting said saddle points for said tooth, said line or lines comprising a transition between teeth and gingival tissue and between adjacent teeth in said model.

12. The improvement of claim 11, wherein said instructions 4) comprise instructions:
   a) performing a directional ravine detection process testing for paths between saddle points with a concave curvature between two saddle points; and
   b) delimiting an area bounded by said paths if said ravine detection process is successful.

13. In a system comprising a programmed computer containing instructions for separating virtual teeth from a virtual model of both teeth and gingival tissue, the improvement comprising:
   providing instructions for execution by said programmed computer that identifies a path interconnecting saddle points between teeth, said path comprising a transition between teeth and gingival tissue and between adjacent teeth in said model, wherein said path is identified by performing a tree search tracing paths along a surface of said virtual model between said saddle points and selecting a path from said paths in said tree search based on a quality values assigned to said paths.

14. The improvement of claim 13, wherein said tree search is performed by reference to local curvature of said virtual model and a vector field for said model defining a direction of search for said path.

* * * * *